(12) United States Patent
Eidenschink et al.

(10) Patent No.: US 7,922,753 B2
(45) Date of Patent: *Apr. 12, 2011

(54) BIFURCATED STENT DELIVERY SYSTEM

(75) Inventors: Tracee Eidenschink, Wayzata, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 669 days.

This patent is subject to a terminal disclaimer.

(21) Appl. No.: 10/757,646

(22) Filed: Jan. 13, 2004

(65) Prior Publication Data

US 2005/0154442 A1   Jul. 14, 2005

(51) Int. Cl.
*A61F 2/84* (2006.01)
(52) U.S. Cl. ..................................... 623/1.11
(58) Field of Classification Search ............... 606/194, 606/108; 623/1.11, 1.12, 1.35, 1.42, 1.46, 623/1.23
See application file for complete search history.

(56) References Cited

U.S. PATENT DOCUMENTS

| | | | |
|---|---|---|---|
| 4,448,195 A | 5/1984 | Leveen et al. | 128/344 |
| 4,484,585 A | 11/1984 | Baier | 128/748 |
| 4,601,701 A | 7/1986 | Mueller, Jr. | 604/83 |
| 4,769,005 A | 9/1988 | Ginsburg et al. | 604/53 |
| 4,776,337 A | 10/1988 | Palmaz | 128/343 |
| 4,913,141 A | 4/1990 | Hillstead | 606/108 |
| 4,994,071 A | 2/1991 | MacGregor | 606/194 |
| 4,998,923 A | 3/1991 | Samson et al. | 606/194 |
| 5,019,085 A | 5/1991 | Hillstead | 606/108 |
| 5,120,308 A | 6/1992 | Hess | |
| 5,122,154 A | 6/1992 | Rhodes | 606/198 |
| 5,195,984 A | 3/1993 | Schatz | 606/195 |
| 5,219,335 A | 6/1993 | Willard et al. | |
| 5,219,355 A | 6/1993 | Parodi et al. | 606/191 |
| 5,246,421 A | 9/1993 | Saab | |
| 5,257,974 A * | 11/1993 | Cox | 604/103.05 |
| 5,316,023 A | 5/1994 | Palmaz et al. | 128/898 |
| 5,380,299 A | 1/1995 | Fearnot et al. | |
| 5,397,305 A | 3/1995 | Kawula et al. | 604/96 |
| 5,449,343 A | 9/1995 | Samson et al. | |
| 5,449,382 A | 9/1995 | Dayton | |
| 5,477,856 A | 12/1995 | Lundquist | |
| 5,556,413 A | 9/1996 | Lam | |
| 5,571,086 A | 11/1996 | Kaplan et al. | 604/96 |
| 5,609,627 A | 3/1997 | Goicoechea et al. | 623/1 |
| 5,632,763 A | 5/1997 | Glastra | |
| 5,634,901 A * | 6/1997 | Alba et al. | 604/96.01 |

(Continued)

FOREIGN PATENT DOCUMENTS

CA    2517380    9/2004

(Continued)

OTHER PUBLICATIONS

Noveon, www.estane.com, Medical Urethanes Overview.*

(Continued)

*Primary Examiner* — (Jackie) Tan-Uyen T Ho
*Assistant Examiner* — Ryan Severson
(74) *Attorney, Agent, or Firm* — Seager, Tufte & Wickhem, LLC

(57) ABSTRACT

A catheter assembly comprises a catheter which includes a catheter shaft and a balloon positioned thereon. A rotatable sheath is rotatably disposed about a portion of the catheter. The rotatable sheath has a first portion inner diameter and a second portion inner diameter, which are different.

42 Claims, 16 Drawing Sheets

U.S. PATENT DOCUMENTS

| | | |
|---|---|---|
| 5,643,278 A | 7/1997 | Wijay |
| 5,670,161 A * | 9/1997 | Healy et al. ............... 623/1.42 |
| 5,683,345 A | 11/1997 | Waksman et al. |
| 5,697,971 A | 12/1997 | Fischell et al. |
| 5,725,519 A | 3/1998 | Penner et al. |
| 5,744,515 A * | 4/1998 | Clapper ................... 523/113 |
| 5,749,825 A * | 5/1998 | Fischell et al. ................ 600/3 |
| 5,755,734 A | 5/1998 | Richter et al. |
| 5,755,735 A | 5/1998 | Richter et al. |
| 5,755,778 A | 5/1998 | Kleshinski |
| 5,772,669 A | 6/1998 | Vrba |
| 5,776,141 A | 7/1998 | Klein et al. |
| 5,797,952 A | 8/1998 | Klein |
| 5,817,100 A | 10/1998 | Igaki |
| 5,824,055 A | 10/1998 | Spiridigliozzi et al. .......... 623/1 |
| 5,836,952 A | 11/1998 | Davis et al. |
| 5,843,027 A * | 12/1998 | Stone et al. ................. 604/509 |
| 5,873,906 A | 2/1999 | Lau et al. |
| 5,876,374 A | 3/1999 | Alba et al. |
| 5,893,868 A | 4/1999 | Hanson et al. |
| 5,906,640 A | 5/1999 | Penn et al. |
| 5,908,405 A | 6/1999 | Imran et al. |
| 5,921,995 A | 7/1999 | Kleshinski |
| 5,935,161 A | 8/1999 | Robinson et al. |
| 5,941,908 A | 8/1999 | Goldsteen et al. |
| 5,951,569 A | 9/1999 | Tuckey et al. |
| 5,957,929 A | 9/1999 | Brenneman |
| 5,961,546 A | 10/1999 | Robinson et al. |
| 5,961,548 A | 10/1999 | Shmulewitz |
| 6,013,092 A | 1/2000 | Dehdashtian et al. |
| 6,015,424 A | 1/2000 | Rosenbluth et al. |
| 6,017,362 A | 1/2000 | Lau ............................. 623/1 |
| 6,027,460 A | 2/2000 | Shturman .................. 600/585 |
| 6,033,434 A | 3/2000 | Borghi ......................... 623/1 |
| 6,048,350 A * | 4/2000 | Vrba ......................... 623/1.11 |
| 6,048,361 A | 4/2000 | Von Oepen ................... 623/1 |
| 6,056,722 A | 5/2000 | Jayaraman .................. 604/102 |
| 6,056,775 A | 5/2000 | Borghi et al. .............. 623/1.16 |
| 6,059,813 A | 5/2000 | Vrba et al. ................. 606/198 |
| 6,071,286 A | 6/2000 | Mawad ...................... 606/108 |
| 6,077,297 A | 6/2000 | Robinson et al. ........... 623/1.11 |
| 6,090,127 A | 7/2000 | Globerman ................ 606/194 |
| 6,096,073 A | 8/2000 | Webster et al. ............ 623/1.16 |
| 6,099,497 A | 8/2000 | Adams et al. ............. 604/96.01 |
| 6,110,191 A | 8/2000 | Dehdashtian et al. ........ 606/192 |
| 6,117,156 A | 9/2000 | Richter et al. .............. 606/194 |
| 6,120,522 A | 9/2000 | Vrba et al. .................. 606/190 |
| 6,132,450 A | 10/2000 | Hanson et al. .............. 606/198 |
| 6,143,014 A | 11/2000 | Dehdashtian et al. ........ 606/192 |
| 6,146,415 A | 11/2000 | Fitz ............................ 623/1.11 |
| 6,152,944 A | 11/2000 | Holman et al. ............ 623/1.11 |
| 6,165,195 A * | 12/2000 | Wilson et al. .............. 606/194 |
| 6,165,196 A | 12/2000 | Stack et al. |
| 6,165,210 A | 12/2000 | Lau et al. ................... 623/1.12 |
| 6,187,015 B1 | 2/2001 | Brenneman ................ 606/108 |
| 6,190,360 B1 | 2/2001 | Iancea et al. .............. 604/164.09 |
| 6,190,393 B1 | 2/2001 | Bevier et al. .............. 606/108 |
| 6,210,380 B1 | 4/2001 | Mauch ....................... 604/284 |
| 6,210,431 B1 | 4/2001 | Power .......................... 623/1.11 |
| 6,221,090 B1 | 4/2001 | Wilson ....................... 606/194 |
| 6,221,097 B1 | 4/2001 | Wang et al. ................ 623/1.11 |
| 6,224,587 B1 | 5/2001 | Gibson ....................... 604/528 |
| 6,238,410 B1 | 5/2001 | Vrba et al. .................. 606/198 |
| 6,246,914 B1 | 6/2001 | De la Rama et al. ........ 607/122 |
| 6,254,593 B1 | 7/2001 | Wilson ....................... 606/1.11 |
| 6,258,052 B1 | 7/2001 | Milo ............................. 604/22 |
| 6,258,073 B1 | 7/2001 | Mauch ....................... 604/284 |
| 6,264,688 B1 | 7/2001 | Herklotz et al. ........... 623/1.16 |
| 6,280,466 B1 | 8/2001 | Kugler et al. ............. 623/1.12 |
| 6,287,277 B1 | 9/2001 | Yan ........................... 604/96.01 |
| 6,287,330 B1 | 9/2001 | Johansson et al. .......... 623/1.13 |
| 6,290,673 B1 | 9/2001 | Shanley ................... 604/102.02 |
| 6,299,636 B1 | 10/2001 | Schmitt et al. ............. 623/1.2 |
| 6,302,906 B1 | 10/2001 | Goicoechea et al. ........ 623/1.11 |
| 6,319,275 B1 | 11/2001 | Lashinski et al. ........... 623/1.11 |
| 6,322,548 B1 | 11/2001 | Payne et al. ................ 604/500 |
| 6,350,278 B1 * | 2/2002 | Lenker et al. ............. 623/1.12 |
| 6,361,544 B1 | 3/2002 | Wilson et al. ............. 606/194 |
| 6,361,555 B1 | 3/2002 | Wilson ....................... 623/1.11 |
| 6,364,893 B1 | 4/2002 | Sahatjian et al. ........... 606/194 |
| 6,371,978 B1 | 4/2002 | Wilson ....................... 623/1.11 |
| 6,375,660 B1 | 4/2002 | Fischell et al. ............. 606/108 |
| 6,379,372 B1 | 4/2002 | Dehdashtian et al. ........ 606/192 |
| 6,387,120 B2 | 5/2002 | Wilson et al. ............. 623/1.11 |
| 6,391,050 B1 | 5/2002 | Broome ..................... 623/1.11 |
| 6,406,487 B2 | 6/2002 | Brenneman ................ 623/1.11 |
| 6,406,489 B1 | 6/2002 | Richter et al. ............. 623/1.16 |
| 6,416,529 B1 | 7/2002 | Holman et al. ............ 606/194 |
| 6,436,104 B2 | 8/2002 | Hojeibane ................. 606/108 |
| 6,443,980 B1 | 9/2002 | Wang et al. ................ 623/1.35 |
| 6,471,672 B1 | 10/2002 | Brown et al. |
| 6,475,166 B1 | 11/2002 | Escano ....................... 600/585 |
| 6,482,211 B1 | 11/2002 | Choi .......................... 606/108 |
| 6,488,694 B1 | 12/2002 | Lau et al. ................... 606/194 |
| 6,508,835 B1 | 1/2003 | Shaolian et al. ............ 623/1.35 |
| 6,514,281 B1 | 2/2003 | Blaeser et al. ............. 623/1.12 |
| 6,520,983 B1 | 2/2003 | Colgan et al. ............. 623/1.11 |
| 6,520,988 B1 | 2/2003 | Colombo et al. ........... 623/1.35 |
| 6,530,947 B1 | 3/2003 | Euteneuer et al. .......... 623/1.11 |
| 6,533,805 B1 | 3/2003 | Jervis ........................ 623/1.11 |
| 6,540,719 B2 | 4/2003 | Bigus et al. .............. 604/96.01 |
| 6,554,841 B1 | 4/2003 | Yang .......................... 606/108 |
| 6,569,180 B1 | 5/2003 | Sirhan et al. |
| 6,582,459 B1 | 6/2003 | Lau et al. ................... 623/1.11 |
| 6,589,262 B1 | 7/2003 | Honebrink et al. ........... 606/191 |
| 6,596,020 B2 | 7/2003 | Vardi et al. ................ 623/1.11 |
| 6,599,315 B2 | 7/2003 | Wilson ....................... 623/1.11 |
| 6,602,226 B1 | 8/2003 | Smith et al. .............. 604/103.05 |
| 6,607,506 B2 | 8/2003 | Kletschka ................. 604/96.01 |
| 6,613,067 B1 | 9/2003 | Johnson ...................... 606/194 |
| 6,629,981 B2 | 10/2003 | Bui et al. ................... 606/108 |
| 6,660,030 B2 | 12/2003 | Shaolian et al. ............ 623/1.11 |
| 6,669,718 B2 | 12/2003 | Basselink ................... 623/1.11 |
| 6,692,483 B2 | 2/2004 | Vardi et al. ................ 604/529 |
| 6,872,215 B2 | 3/2005 | Crocker et al. |
| 7,070,613 B2 | 7/2006 | Weber et al. |
| 7,238,197 B2 | 7/2007 | Sequin et al. |
| 2001/0049548 A1 | 12/2001 | Vardi et al. ................ 623/1.11 |
| 2002/0019664 A1 | 2/2002 | Douglas ..................... 623/1.35 |
| 2002/0019665 A1 | 2/2002 | Dehdashtian et al. ........ 623/1.35 |
| 2002/0022874 A1 | 2/2002 | Wilson ....................... 623/1.11 |
| 2002/0038140 A1 | 3/2002 | Yang et al. ................ 623/1.12 |
| 2002/0038141 A1 | 3/2002 | Yang et al. ................ 623/1.12 |
| 2002/0052640 A1* | 5/2002 | Bigus et al. ............... 623/1.11 |
| 2002/0072755 A1 | 6/2002 | Bigus et al. ............... 606/108 |
| 2002/0111675 A1 | 8/2002 | Wilson ....................... 623/1.35 |
| 2002/0116045 A1 | 8/2002 | Eidenschink ............... 623/1.11 |
| 2002/0120320 A1 | 8/2002 | Wang et al. ................ 623/1.11 |
| 2002/0165598 A1 | 11/2002 | Wahr et al. |
| 2003/0023298 A1 | 1/2003 | Jervis ........................ 623/1.11 |
| 2003/0055483 A1 | 3/2003 | Gumm ....................... 623/1.11 |
| 2003/0055484 A1 | 3/2003 | Lau et al. ................... 623/1.13 |
| 2003/0130716 A1 | 7/2003 | Weber et al. |
| 2003/0181923 A1 | 9/2003 | Vardi ......................... 606/108 |
| 2003/0195546 A1 | 10/2003 | Solar et al. ................ 606/192 |
| 2004/0172119 A1 | 9/2004 | Eidenschink |
| 2005/0149161 A1* | 7/2005 | Eidenschink et al. ........ 623/1.11 |
| 2005/0154442 A1 | 7/2005 | Eidenschink et al. |
| 2005/0273149 A1 | 12/2005 | Tran et al. |
| 2008/0119923 A1 | 5/2008 | Tran et al. |

FOREIGN PATENT DOCUMENTS

| | | |
|---|---|---|
| CA | 2533306 | 3/2005 |
| CA | 2556693 | 9/2005 |
| CA | 2569567 | 12/2005 |
| DE | 297 01 758 | 5/1997 |
| EP | 1601312 | 9/2007 |
| FR | 2 678 508 A1 | 1/1993 |
| WO | 00/44307 | 8/2000 |
| WO | 03/017872 | 3/2003 |
| WO | 03/017872 A1 | 3/2003 |
| WO | 03/055414 | 7/2003 |
| WO | 03/061529 | 7/2003 |
| WO | 2004/075792 | 9/2004 |
| WO | 2005025458 | 3/2005 |
| WO | 2005067818 | 7/2005 |

| WO | 2005070334 | 8/2005 |
| WO | 2005079902 | 9/2005 |
| WO | 2005122958 | 12/2005 |

OTHER PUBLICATIONS

U.S. Appl. No. 10/657,472, filed Sep. 8, 2003, Eidenschink, et al.
U.S. Appl. No. 10/780,937, filed Feb. 18, 2004, Eidenschink, et al.
U.S. Appl. No. 10/784,337, filed Feb. 23, 2004, Eidenschink, et al.
U.S. Appl. No. 10/863,724, filed Jun. 8, 2004, Eidenschink, et al.
Foley et al., "Bifurcation Lesion Stenting", *The Thoraxcentre Journal*, vol. 8, No. 4, (1996).
Schampaert, MD, Erick et al., "The V-Stent: A Novel Technique for Coronary Bifurcation Stenting", *Catheterization and Cardiovascular Diagnosis*, 39:320-326 (1996).
Pomerantz, MD, et al., "Distortion of Palmaz-Schatz Stent Geometry Following Side-Branch Balloon Dilation Through the Stent in a Rabbit Model", *Catheterization and Cardiovascular Diagnosis*, 40:422-426 (1997).
Palmaz, MD, et al., "Aortic Bifurcation Stenosis: Treatment with Intravascular Stents", *Journal of Vascular and Interventional Radiology*, vol. 2, No. 3, pp. 319-323 (Aug. 1991).
Oda, MD., et al., "Fork Stenting for Bifurcational Lesion", Journal of Interventional Cardiology, vol. 9, No. 6, pp. 445-454 (Dec. 1996).
Nakamura et al., "Techniques for Palmaz-Schatz Stent Deployment in Lesions With a Large Side Branch", Catheterization and Cardiovascular Diagnosis, vol. 34, pp. 353-361 (1995).
U.S. Appl. No. 10/375,689, filed Feb. 27, 2003, Eidenschink.
U.S. Appl. No. 10/747,546, filed Dec. 29, 2003, Eidenschink et al.

* cited by examiner

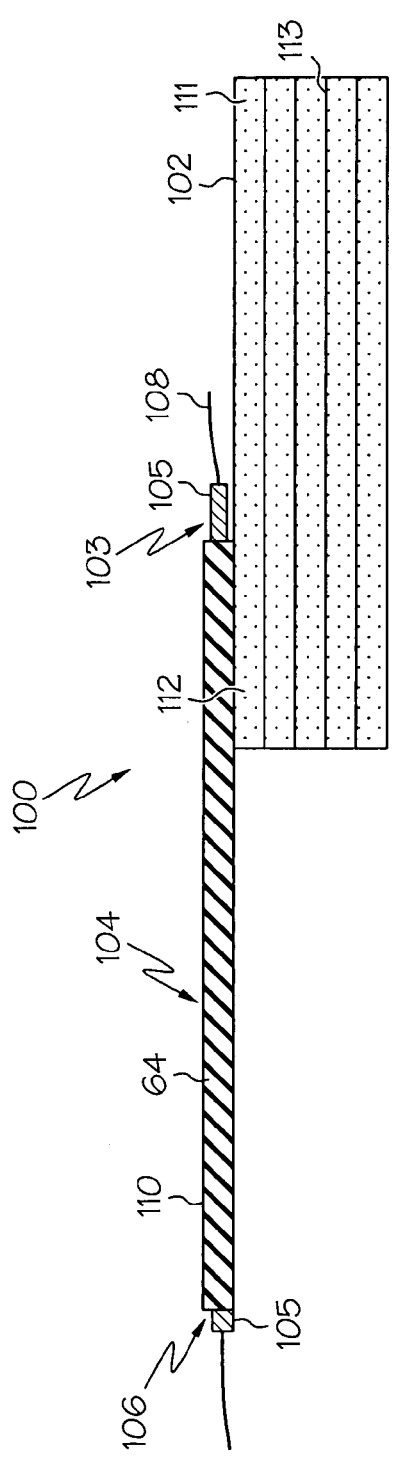
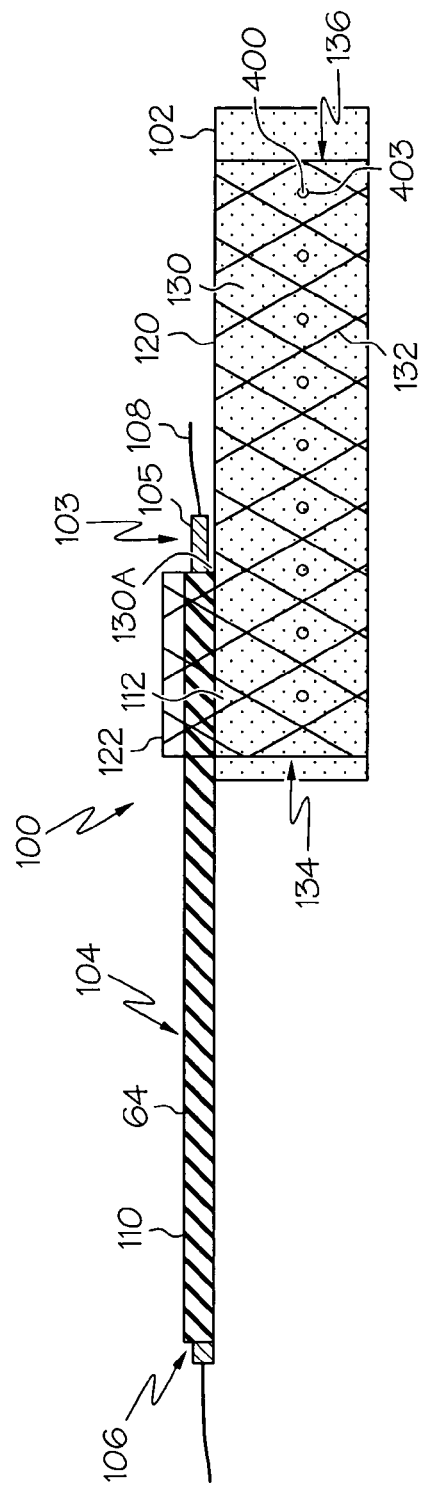
FIG. 1
FIG. 2

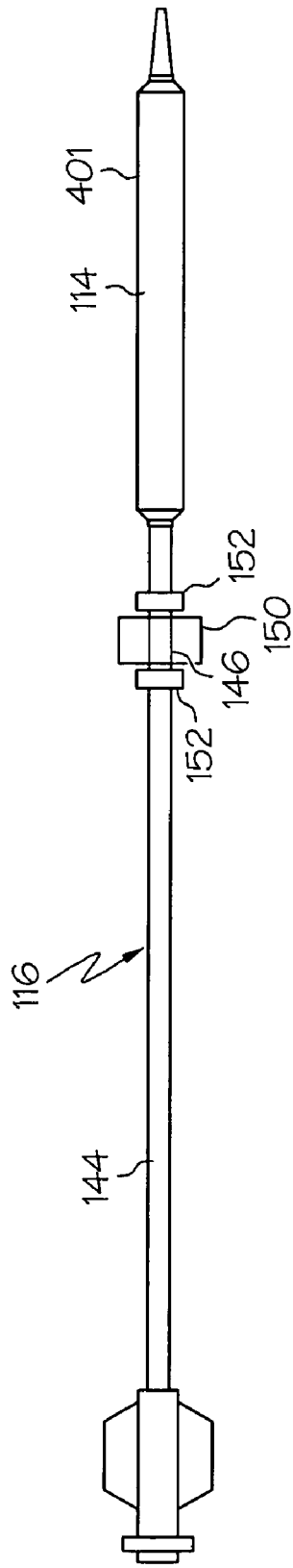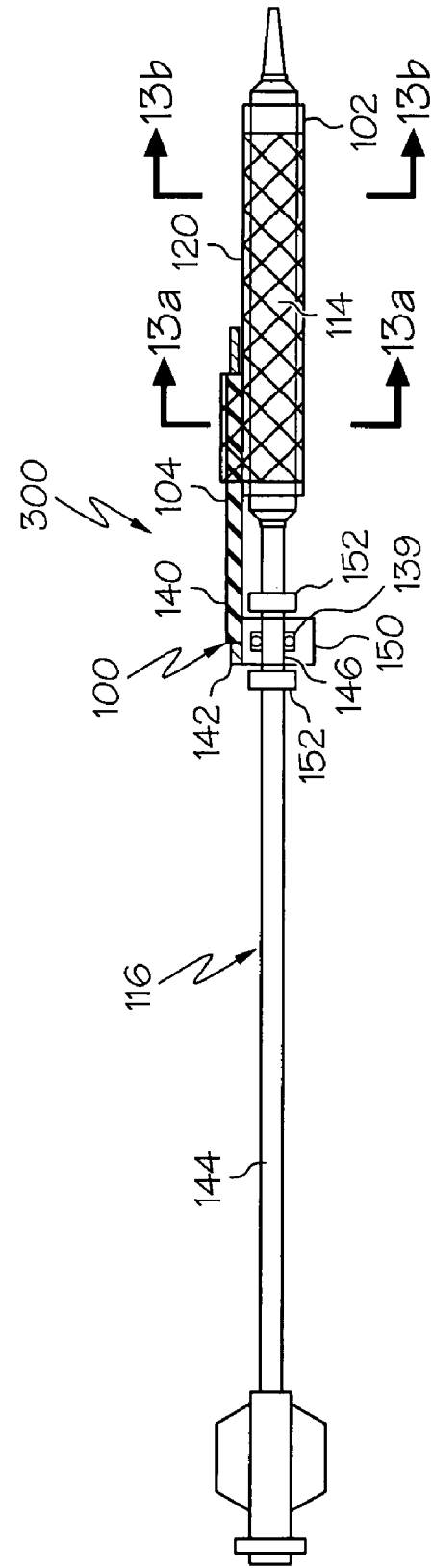

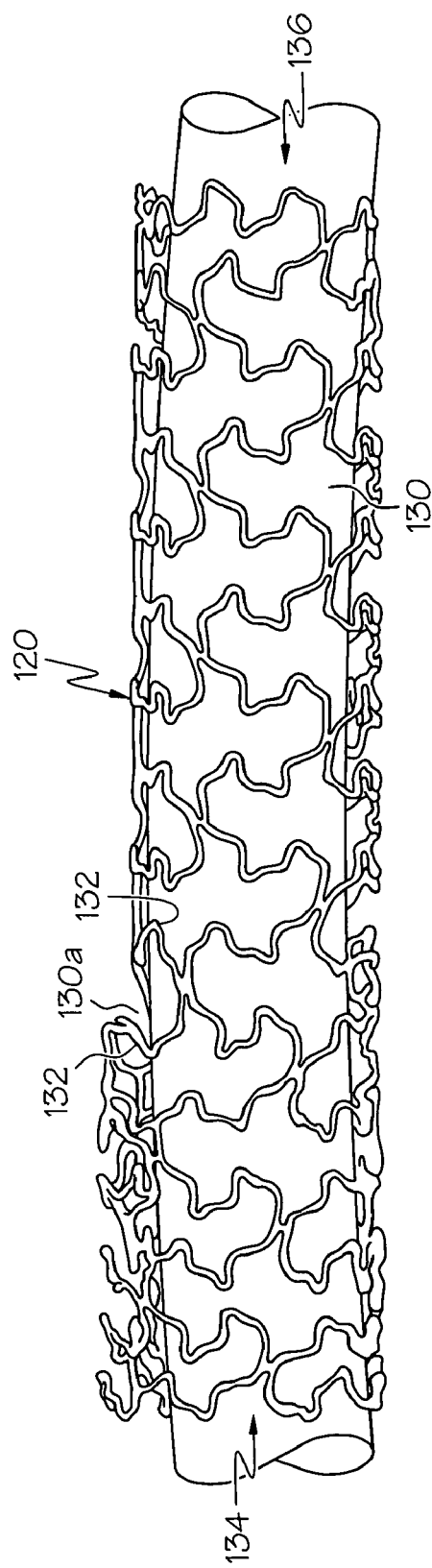
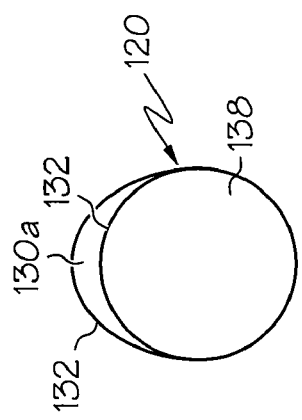
FIG. 7
FIG. 8

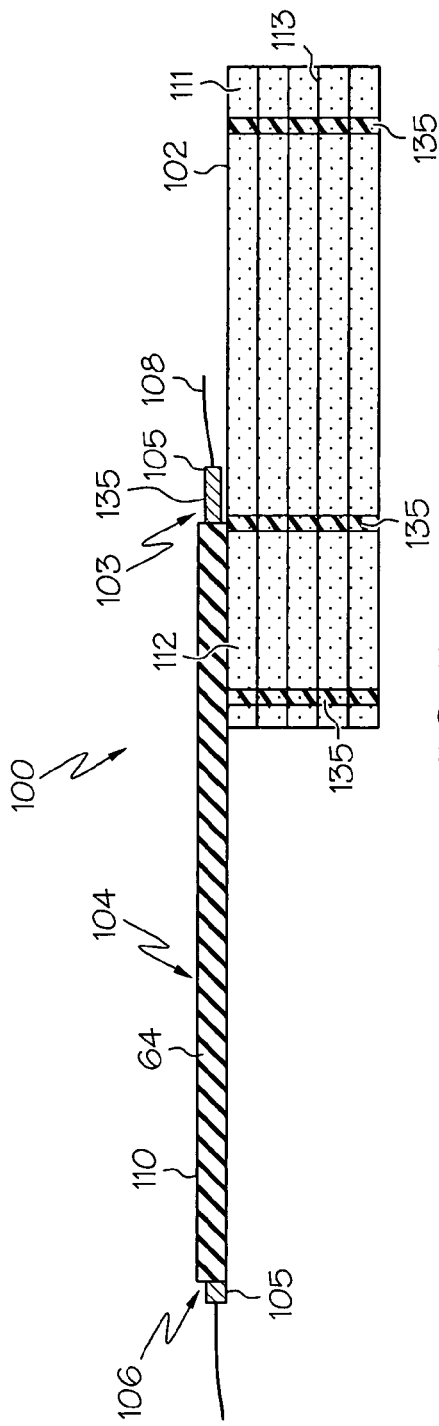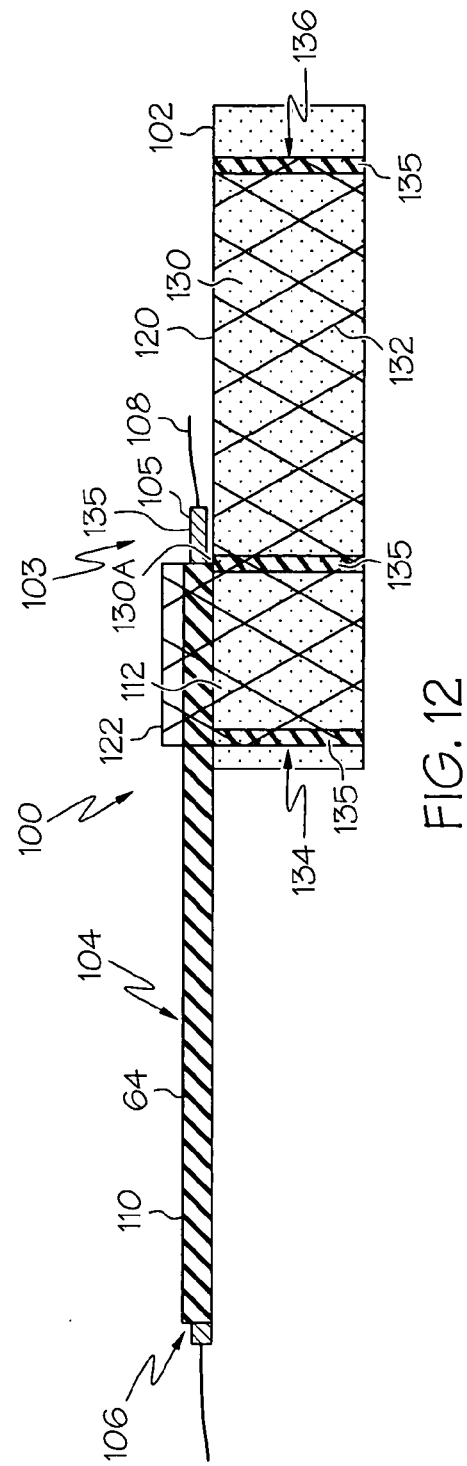

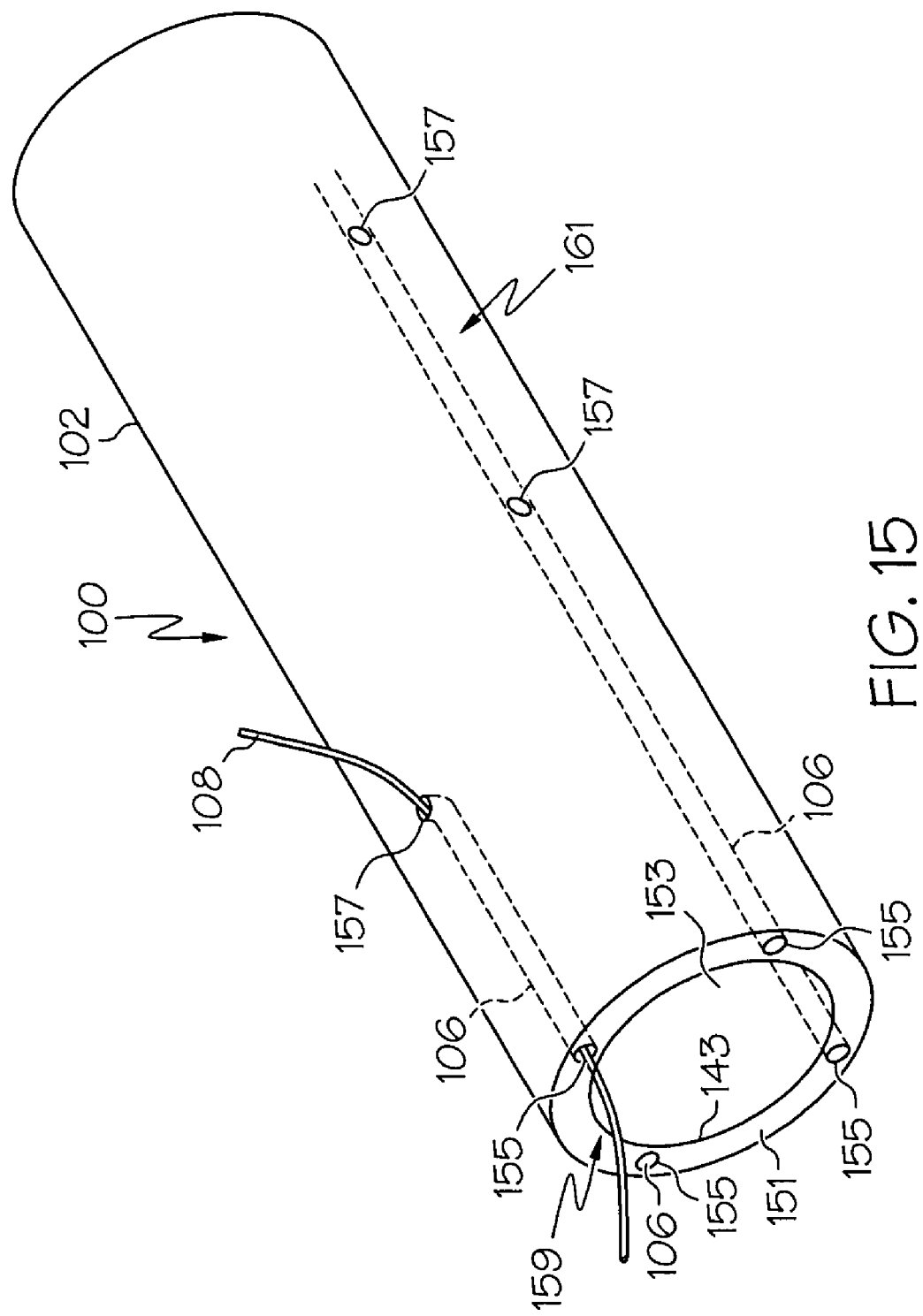

BIFURCATED STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

A stent delivery system employing a stent assembly with branches intended for deployment in the adjacent branches of a vessel bifurcation has been proposed to allow placement of a portion of the assembly in both a primary passage, such as an artery, and a secondary passage, such as a side branch artery. Additionally, these stents generally have an opening which allows for unimpeded blood flow into the side branch artery. However, problems are still encountered in orienting the stent relative to the side branch at the bifurcation of the primary and secondary passages. Moreover, such bifurcated assemblies are typically specially manufactured at an increased cost over a more standard stent intended for single vessel deployment.

In delivering a stent to a vessel location, many current devices rely on either passive torque (e.g., pushing the stent forward and allowing the stent that is fixed on the guidewire/ balloon to passively rotate itself into place) or creating torque from outside of the patient to properly orient the medical device in the passage. These devices and methods of achieving proper angular orientation have not been shown to be effective in properly placing and positioning the stent.

Thus, a need exists to provide a catheter which is capable of allowing a medical device such as a stent to be easily maneuvered and aligned at a vessel bifurcation or other location, while also adequately protecting the catheter and/or balloon to which the stent is mounted. Various devices and methods described herein address this need by providing a catheter system with a rotatable sheath apparatus which a stent may be mounted on or engaged to. The rotatable assembly is rotatable about the catheter shaft thereby eliminating the need to apply torque to the catheter shaft to align the stent at a vessel bifurcation.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Some embodiments of the present invention include a freely rotating deployment assembly for a stent assembly for maintaining side branch access and protection.

In some embodiments the invention is directed to a rotatable catheter assembly which comprises a catheter about which a stent, prior to delivery is freely rotatable. The stent maintains its position relative to the catheter by engagement to a rotatable collar positioned proximal to the stent.

In some embodiments at least a proximal end of the stent is engaged by an engagement mechanism to the rotatable collar that is located proximal to the stent. The catheter assembly constructed and arranged to release the stent from the collar to deliver the stent. In some embodiments the engagement mechanism comprises one or more engagement members constructed from a shape memory material and/or an electroactive polymer (EAP). In some embodiments the one or more engagement members are at bio-absorbable. In some embodiments the one or more engagement members are mechanically actuatable from an engaged position, wherein the stent remains secured to the collar, to a release position, wherein the stent is freed from the collar.

In at least some embodiments the catheter comprises a balloon about which the stent is rotatably mounted prior to delivery. In some embodiments at least a portion of the balloon is coated with a lubricious substance. In some embodiments a protective covering is interposed between the balloon and the stent. In at least one embodiment the covering is an expandable layer of material.

At least one embodiment of the invention is directed to alternative configurations of rotatable sheath mechanisms such as are described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery, the entire content of both being incorporated herein by reference.

In some embodiments the invention is directed to a rotatable sheath having a sheath wall having a predetermined thickness, the sheath wall defining at least one lumen which extends through at least a portion of the length of the sheath.

In some embodiments the thickness of the sheath wall is variable such that the inner diameter of the sheath is variable and/or non-circular and the outer diameter of the sheath is substantially constant and/or circular.

In some embodiments the sheath comprises one or more bands or areas of radiopaque material and/or material detectable by imaging modalities such as X-Ray, MRI or ultrasound. Such material(s) may be in the form of a coating.

In some embodiments the sheath has a nominal state wherein when the sheath is in the nominal state the outer diameter of the sheath has a first diameter that is substantially constant throughout the length of the sheath; a loading state wherein when the stent is being loaded onto the sheath the outer diameter of the sheath has a second diameter less than first diameter; and a loaded state wherein once the stent is loaded onto the sheath the outer diameter of the sheath is variable along the length of the sheath. In some embodiments, when the sheath is in the loaded state at least a first portion of the outer diameter of the sheath is in the first diameter and at least a second portion of the outer diameter of the sheath is in a third diameter. In some embodiments the third diameter is less than the first diameter and in some embodiments the third diameter is greater than the second diameter.

In at least one embodiment the invention is directed to a catheter system employing a balloon, a rotatable sheath is disposed about the balloon. In some embodiments the rotatable sheath has a length which extends over one or both cones of the balloon.

In at least one embodiment the invention is directed to a catheter system employing any of the rotatable sheath configurations described herein.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1 is a side view of a rotating sheath assembly.

FIG. 2 is a side view of the assembly shown in FIG. 1 shown configured for delivery of a stent.

FIG. 3 is a side view of a catheter assembly. The catheter assembly is provided with a rotating collar.

FIG. 4 is a side view of the catheter assembly of FIG. 3 with the rotating sheath assembly and stent of FIG. 2 mounted thereon.

FIG. 7 is a side perspective view of the stent shown in FIG. 6 wherein a side branch opening is shown formed.

FIG. 8 is a cross-sectional view of the stent of FIG. 7.

FIG. 11 is a side view of the rotatable assembly shown in FIG. 1 wherein the sheath is provided with one or more marker bands.

FIG. 12 is a side view of the rotatable assembly shown in FIG. 11 wherein a stent has been disposed thereabout.

FIG. 15 is a perspective view of the sheath shown in FIG. 14.

FIGS. 16a-d depict the formation of a single piece rotatable sheath having two guide wire openings and/or passages therethrough.

Figure 17B:
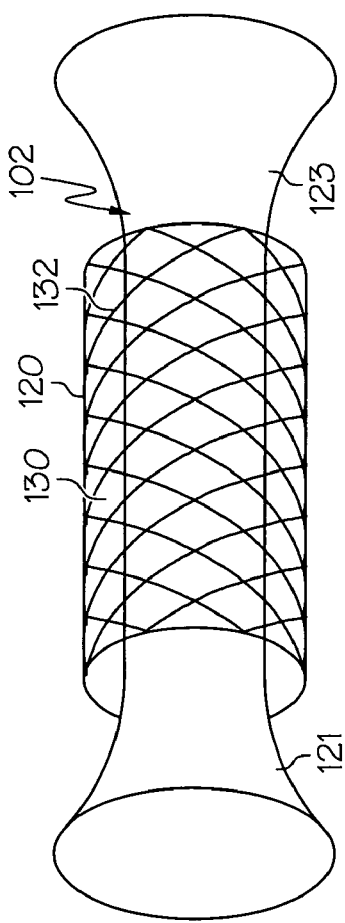
Figure 17A:
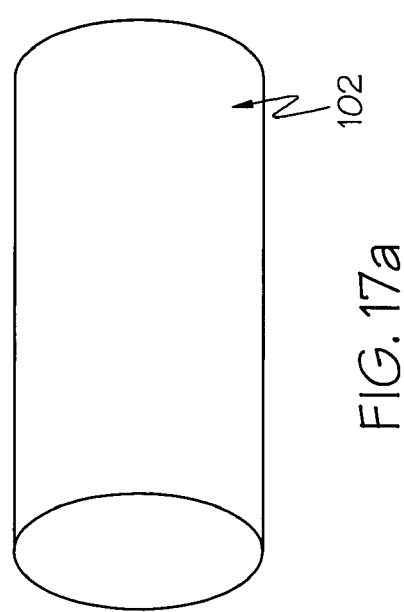

FIG. 17a is a perspective view of a rotatable sheath shown prior to placement of a stent thereabout.

FIG. 17b is a perspective view of the rotatable sheath depicted in FIG. 17a wherein the sheath is shown being stretched or elongated to reduce the diameter of the sheath so a stent may be disposed thereabout.

Figure 17C:
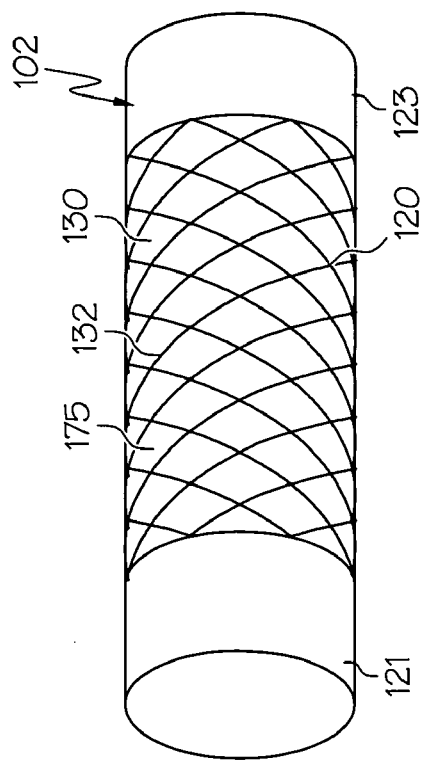

FIG. 17c is a perspective view of the rotatable sheath and stent depicted in FIG. 17b wherein the sheath has been allowed to return to a nominal outer diameter thereby securing the stent thereabout.

Figure 18:
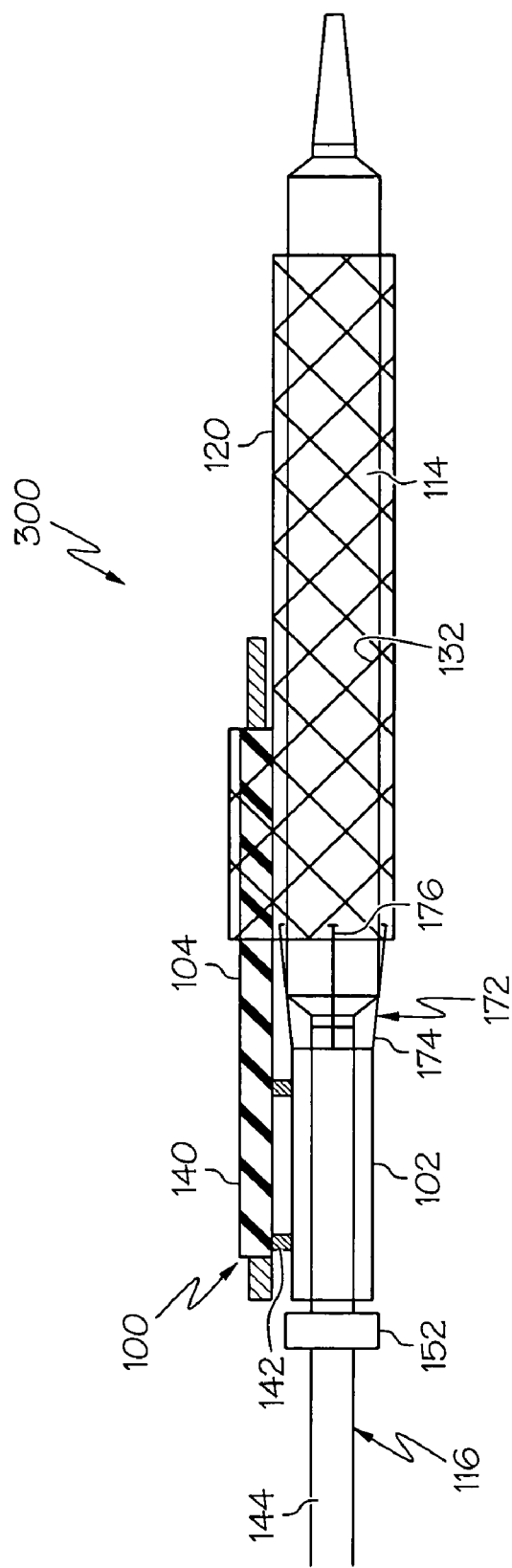

FIG. 18 is a side view of a catheter having a stent which is rotatable relative to the catheter shaft and which is retained thereon prior to delivery by a rotatable assembly having at least one securement member releasably secured to the stent.

Figure 19:
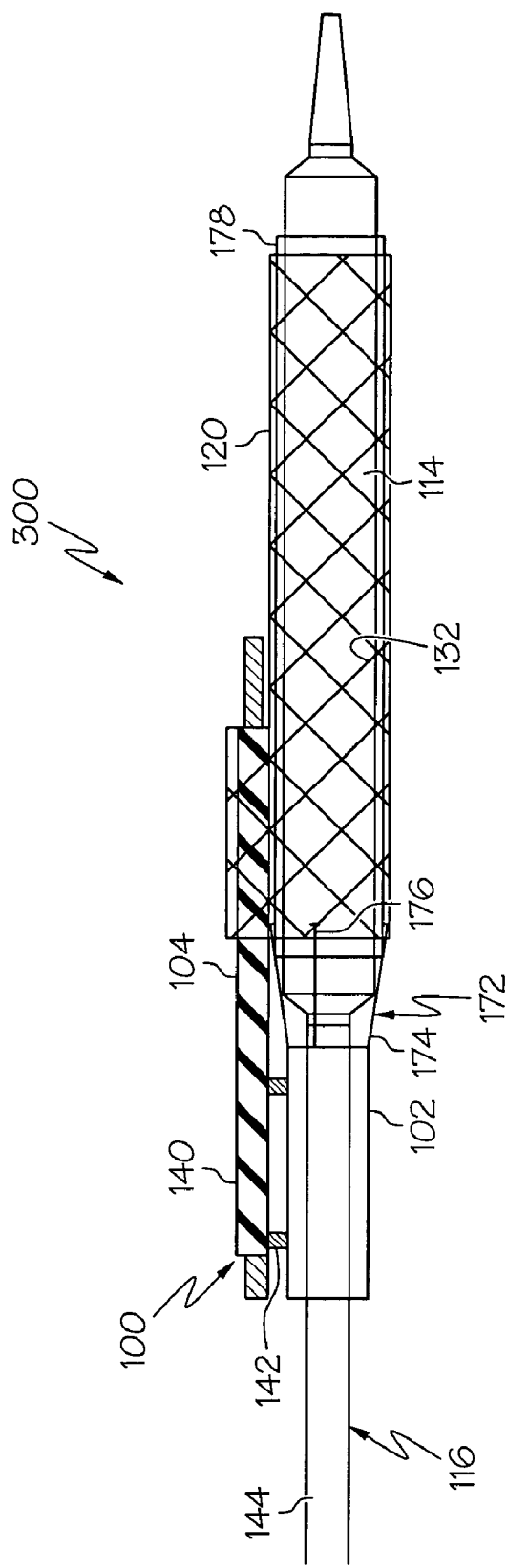

FIG. 19 is a side view of the catheter shown in FIG. 18 wherein a protective sheath is disposed between the balloon and the rotatable stent.

Figure 20:
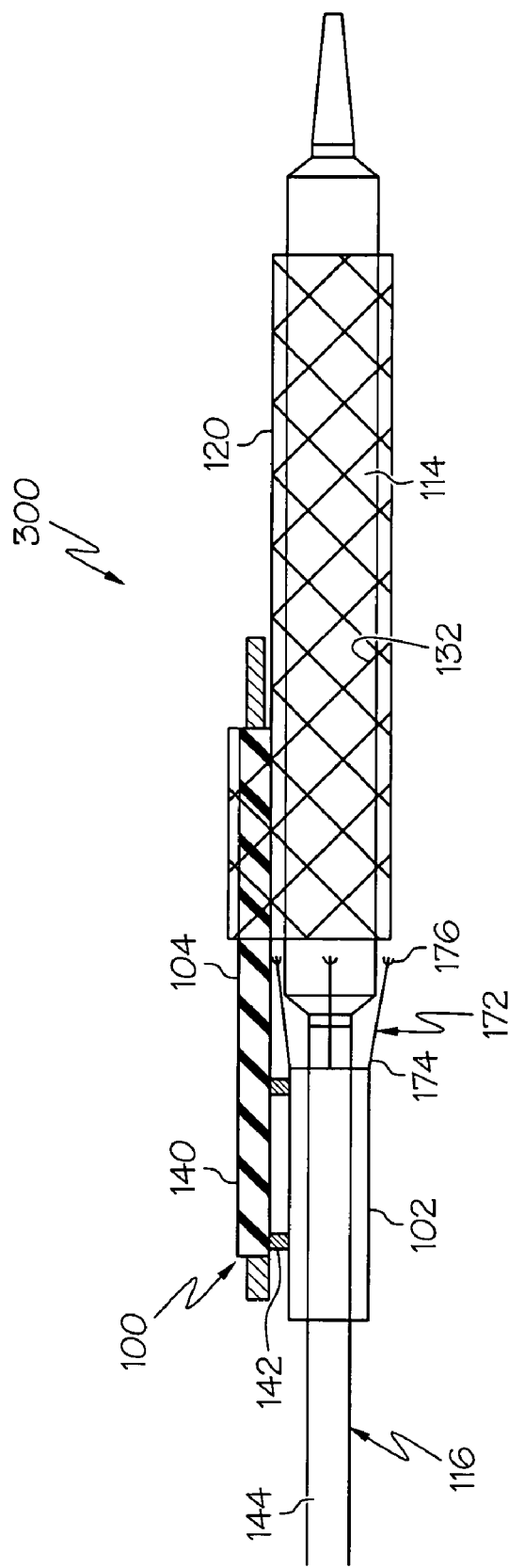

FIG. 20 is a side view of the catheter shown in FIG. 18 wherein the securement members have been activated to release the stent for delivery.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 5:
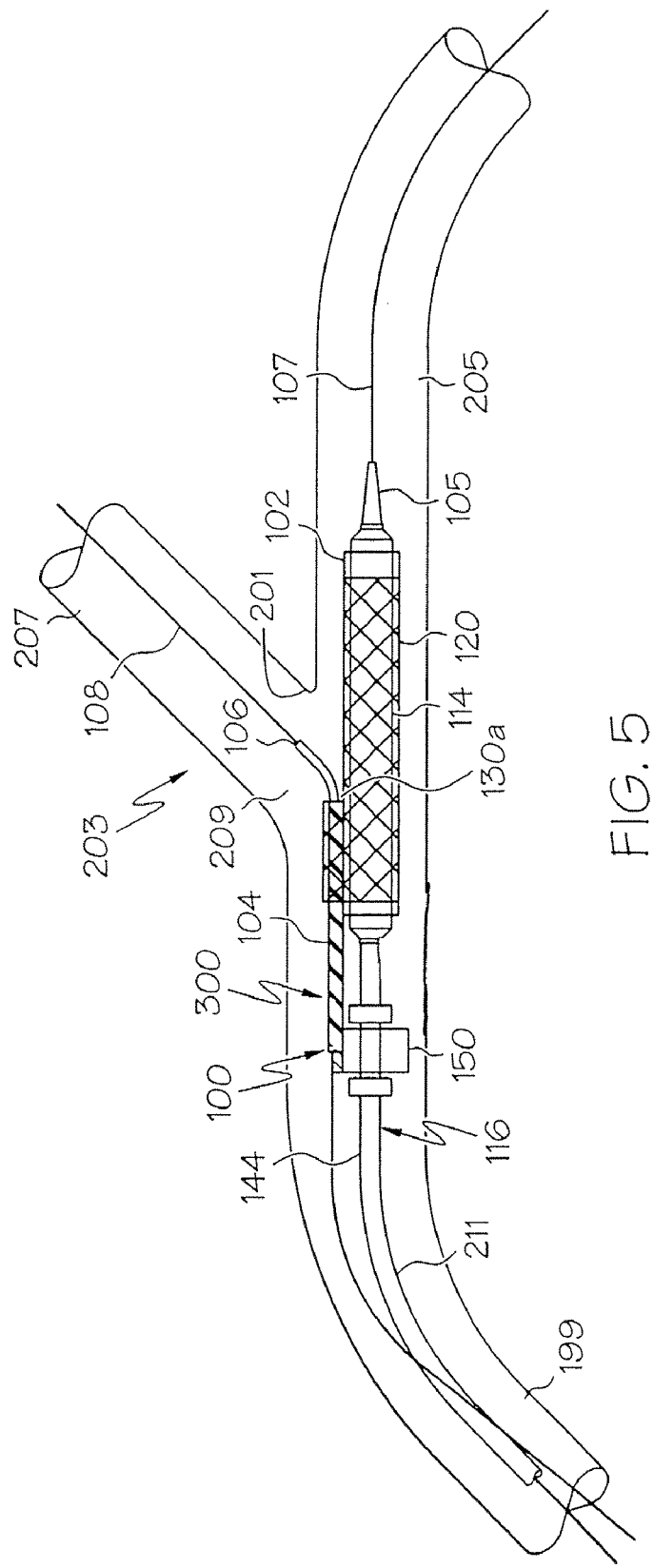
FIG. 5 is a side view of the catheter assembly of FIG. 4 shown being advanced along a guidewire to a vessel bifurcation prior to delivery of the stent.

Referring now to the drawings which are for the purposes of illustrating embodiments of the invention only and not for purposes of limiting same, FIGS. 1-2 illustrate a an assembly 100 for use in a stent delivery system 300 which is mounted on a catheter body 116, such as is depicted in FIGS. 3-5, to provide the system with a rotating region that allows a stent 120, such as is shown in FIGS. 6-9, to be properly aligned in a vessel bifurcation. Some additional examples of such assemblies are shown and described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery and are incorporated herein by reference.

The rotating sheath assembly 100 depicted in FIGS. 1-2 comprises a tubular sleeve or sheath 102 and a positioning or secondary guidewire housing 104. The housing 104 defines a secondary guidewire lumen 106 through which a secondary guidewire 108 may be passed.

Though the housing 104 may be constructed of a wide variety of materials including metal plastic, etc., in some instances the housing 104 may be an external reinforcing member or hypotube 64.

The hypotube 64 may comprise stainless steel one or more polymer materials or other material. To improve flexibility, in some cases the housing 104 is provided with one or more openings 110 along its length. For example, the housing 104 may be spiral cut to provide at least a continuous opening 110 which acts to provide improve the flexibility of the housing 104.

The assembly 100 may include a secondary guidewire housing 104 which further comprises an inner shaft 103, about which the hypotube 64 is disposed. The inner shaft 103 may be a flexible hollow tubular member which extends distally beyond the distal end of the hypotube 64. This distal and/or proximal tips 105 of the inner shaft 103 provides the housing with a flexible protective sheath about the guidewire 108 as it passes out of the secondary guidewire lumen 106. Such a protective covering prevents the guidewire 108 from excessively rubbing against the wall 201 of the vessel 199, such as in the manner depicted in FIG. 5; even where the secondary guidewire 108 exits the secondary lumen 106 at a significant angle. The inner shaft 103 may be constructed of any of a variety of flexible materials such as: PEBAX, nylon, urethane, and/or other materials in a single layer, multi-layer and/or braided configuration.

In many catheters, the shaft 144 of the catheter 116 defines a primary guidewire housing 211 through which a primary guidewire 107 may be advanced. In use, guidewires 107 and 108 are passed through a lumen or other body vessel 209 to a bifurcation 203. Primary guidewire 107 is then advanced into a primary branch of passage 205 of the bifurcation 203 while the secondary guidewire 108 is advanced into the adjacent or secondary branch 207 of the bifurcation 203. As the system is advanced along both guidewires 107 and 108, as a result of the divergent paths defined by the guidewires 107 and 108, the rotatable sleeve 104 will rotate the stent 120 into a desired position so that the secondary opening 130a of the stent is aligned with the secondary passage 207. Where the catheter 116 is a fixed wire system, the use of the primary guidewire is unnecessary.

Examples of the rotating assembly 100 include a distal portion of the housing 104 being engaged to at least a proximal portion of the sheath 102 at an engagement site 112. The manner or mechanism of engagement between the sheath and housing 104 may be by bonding, welding, adhering adhesively engaging, mechanically engaging or otherwise connecting the surfaces of the respective sheath 102 and housing 104.

The sheath 102 is a hollow tube of sheath material that is configured to be placed over the balloon 114 or other region of a catheter 116, such as in the manner illustrated in FIGS. 3 and 4. The sheath 102 is further configured to be rotatable about the catheter shaft and/or balloon 114, even when a stent 120 has been positioned about and/or affixed to the sheath 102.

In order to ensure that the sheath 102 is rotatable about a balloon 114 and/or other region of a catheter, even with a stent 120 crimped on to the sheath 102 and the catheter is being advanced through the a body, the sheath 102 may be constructed of a variety of low friction materials such as PTFE, HDPE, etc. In at least one embodiment the sheath 102 is at least partially constructed of a hydrophilic material, such as hydrophilic polymers such as; TECOPHILIC® material available from Thermedics Polymer Products, a division of VIASYS Healthcare of Wilmington, Mass.; TECOTHANE®, also available from Thermedics Polymer Products; hydrophilic polyurethanes, and/or aliphatic, polyether-based thermoplastic hydrophilic polyurethane; and any other material that provides the sheath 102 with the ability to rotate freely about the balloon 114 when in the "wet" state, such as when the catheter is exposed to body fluids during advancement through a vessel. Suitable sheath materials may also provide the sheath with rotatability in the "dry", or pre-insertion, state, but with the application of a greater amount of force than when in the wet state, such materials are referred to herein as being tecophilic.

A sheath 102 at least partially constructed from tecophilic material provides the sheath 102 with the ability to rotate freely about the balloon 114 when in the "wet" state, such as when the catheter is exposed to body fluids during advancement through a vessel. The tecophilic sheath 102 is also capable of rotation in the "dry", or pre-insertion, state, but with the application of a greater amount of force than when in the wet state.

In some cases the sheath 102 may be constructed of one or multiple materials, in one or more layers. For example, the sheath 102 may comprise an outer layer of a softer material than that of the material used in constructing an inner layer, such as has been previously described. In some embodiments, an example of which is shown in FIG. 1, the sheath 102 may be comprised of a matrix of a first material 111 and have one or more supportive stripes, strands, members or areas of a second supportive material 113 within, external to or internal to such a matrix.

The composition of the sheath 102 material, whether a single, multiple layer or stripe reinforced extrusion may include essentially any appropriate polymer or other suitable materials. Some example of suitable polymers include Hydrophilic Polyurethanes, Aromatic Polyurethanes, Polycarbonate base Aliphatic Polyurethanes, Engineering polyurethane, Elastomeric polyamides, block polyamide/ethers, polyether block amide (PEBA, for example available under the trade name PEBAX), and Silicones, Polyether-ester (for example a polyether-ester elastomer such as Arnitel available from DSM Engineering Plastics), Polyester (for example a polyester elastomer such as Hytrel available from Du Pont), or linear low density polyethylene (for example Rexell).

Example of suitable reinforcing materials whether alone or blended with other materials, mixtures or combination or copolymers include all Polyamides (for example, Durethan available from Bayer or Cristamid available from ELF Atochem), polyethylene (PE). Marlex high-density polyethylene, polyetheretherketone (PEEK), polyimide (PI), and polyetherimide (PEI), liquid crystal polymers (LCP), and Acetal (Delrin or Celcon).

Often the inner surface of the sheath 102 or the outer surface of the balloon 114 may include a coating of one or more low friction materials or include one or more low friction materials in its construction. Such a coating 401 is shown in FIG. 3 on the surface of the balloon 114 before assembly 100 has been placed thereabout, such as is depicted in FIG. 4. Coating 401 may however by placed between the balloon 114 and sheath 102 at any time. Some examples of a suitable coating material include but are not limited to: hydrogel, silicon, and/or BIOSLIDE® available from SciMed Life Systems, Inc. of Maple Grove Minn.

As mentioned above, the sheath 102 is configured to be freely rotatable about a balloon of a catheter even when a stent 120, such as is shown in FIGS. 2 and 4 is crimped onto the sheath 102. When properly positioned on the sheath 102, a proximal portion 122 of the stent 120 is also disposed about at least a portion of the secondary guidewire housing 104. When properly positioned about the sheath 102 and the housing 104, at least a portion of the housing 104 and/or the secondary guidewire 108 extends distally through a cell opening 130 of the stent 120.

Figure 6:
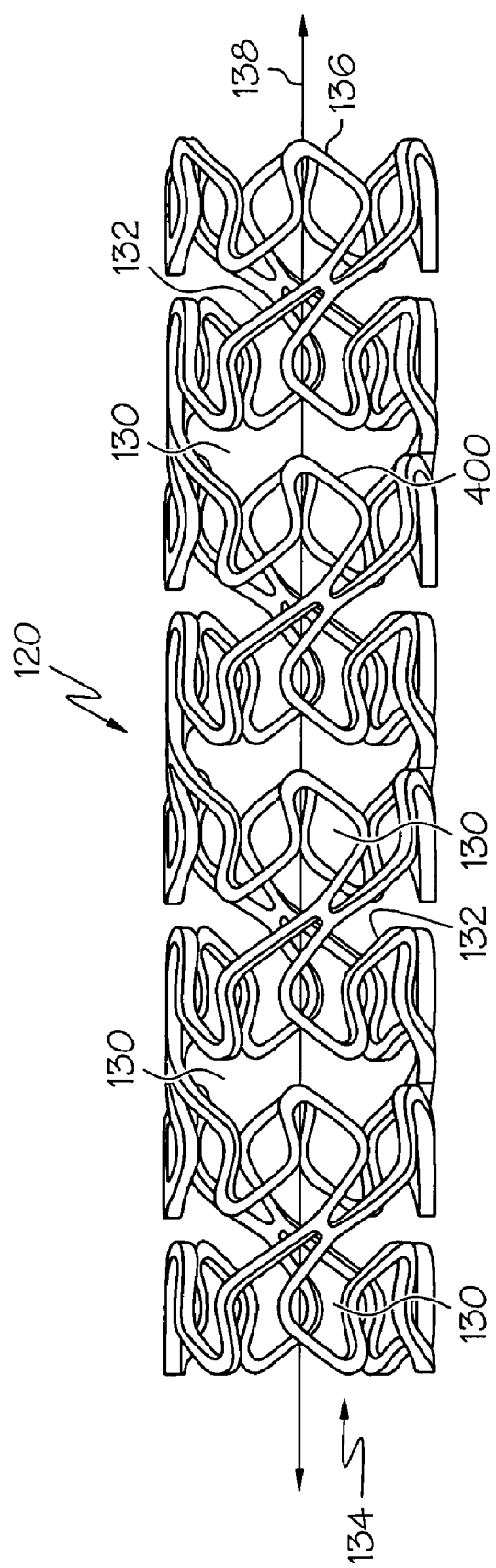
FIG. 6 is a side perspective view of a stent, such as that shown in FIG. 2.

Stent 120 may be a stent, such as is shown in FIG. 6, which is at least partially constructed of a plurality of interconnected struts, connectors or members 132. The stent 132 defines a proximal opening 134, a distal opening 136 and a flow path 138 therebetween. The cell openings 130 are in fluid communication with the flow path 138.

When the secondary guidewire 108 and/or the secondary guidewire housing 104 is threaded through one of the cell openings 130 when the stent is positioned onto the assembly 100, such as is shown in FIGS. 2 and 4, the members 132 that define the selected cell opening 130a, as well as the shape of the opening 130a through which the secondary guidewire 108 exits the stent, may be distorted or modified in order to accommodate the passage of secondary guidewire 108 and/or the secondary guidewire housing 104 therethrough.

The modified cell opening 130a, hereinafter referred to as secondary opening 130a, is positioned on the stent 120 between the proximal opening 134 and the distal opening 136. The manner in which the secondary opening 130a, the members 132 adjacent thereto, and to an extent the stent 120 itself, are modified or distorted by the position of the secondary guidewire and/or secondary guidewire housing is depicted in FIGS. 7 and 8.

It should be noted that when the stent 120 is placed on the assembly in the manner described above, the distortion of the secondary opening 130a and the adjacent members 132 is of a minimal extent, and is provide only to allow sliding passage of the secondary guidewire 108, and if desired a distal portion of the secondary guidewire housing 104, through the secondary opening 130a. As such, the actual size of the secondary opening 130a may be substantially similar, or only marginally different than that of the surrounding cell openings 130.

It should also be further noted that while stent 120 may be a standard "single vessel" stent that is provided with a secondary opening 130a in the manner described above, the stent 120 may also be a bifurcated stent having a trunk or stem portion, with one or more leg portions and/or branch openings adjacent thereto, through one of which the secondary guidewire may be passed. Such bifurcated stents and stent assemblies are well known in the art.

Figure 9:
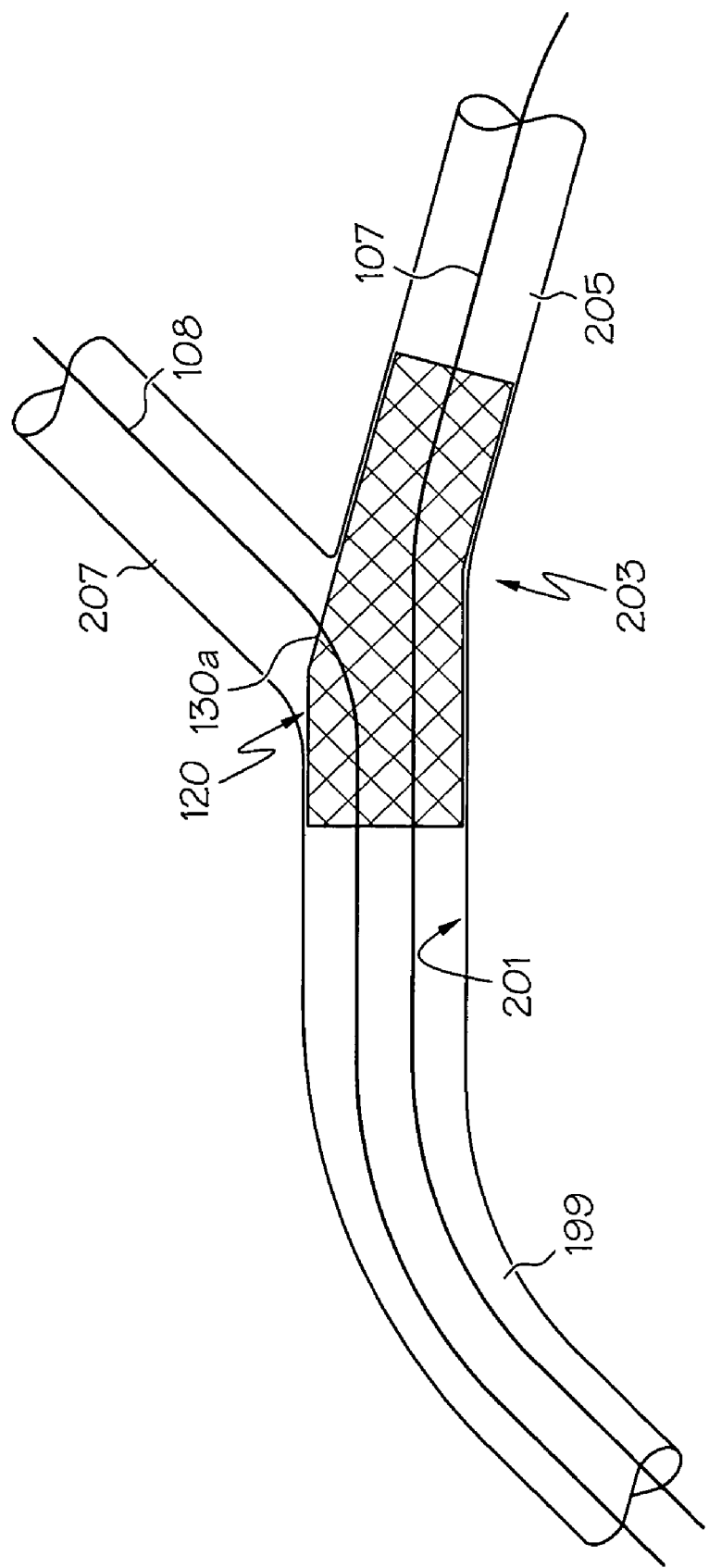
FIG. 9 is a side view of the stent depicted in FIG. 5, wherein the stent has been delivered from the catheter assembly, by balloon expansion and the assembly subsequently withdrawn from the vessel(s).

In some cases, the stent 120, sheath 102 or one or more portions thereof, may be configured to deliver one or more therapeutic agents to a delivery site such as within the vessel 199 or one or more areas adjacent thereto, such as shown in FIGS. 5 and 9.

To better accommodate placement of a therapeutic agent on the stent 120, in some instances one or more stent members 132, such as is shown in FIG. 6, may be configured to include one or more holes, notches, or other surface features to which one or more therapeutic agents 400 may be placed for delivery to the aneurysm site. A therapeutic agent may be placed on the stent in the form of a coating. Often the coating includes at least one therapeutic agent and at least one polymer.

In at least one embodiment, an example of which is shown in FIG. 2, the sheath 102 may include one or more holes, notches, pores, cavities or other surface features 403 wherein one or more therapeutic agents 400 may be positioned. During expansion of the stent 120 the corresponding expansion of the sheath 102 may squeeze or otherwise act to release the agent 400 onto the stent and/or body.

A therapeutic agent may be a drug, a non-genetic agent, a genetic agent, etc. Some examples of suitable non-genetic therapeutic agents include but are not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are $Lin^-$, $Sca-1^+$, $c-Kit^+$, $CD43^+$, $CD45^+$, $CD34^-$.

$Lin^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

$Lin^-CD34^-$—Although $CD34^+$ cells have received much attention, many articles have been published lately which suggest the most primitive bone marrow derived stem cells are $CD34^-$.

$Lin^-CD34^+$—Presence of the cell surface protein CD34 has been used to identify hematopoietic stem cells. However, the marker is also present on progenitor cells and white blood cells of various levels of maturity.

$Lin^-cKit^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the $6^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult Cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In some instances a suitable polymer agent or coating comprises block copolymers comprising at least one A block and at least one B block The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

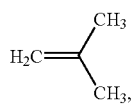

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

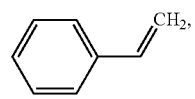

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

Once the stent 120 is positioned on the assembly 100, such as in the manner shown in FIG. 2, the assembly 100 may be slid onto a catheter 116, such as is shown in FIGS. 3-4 so that the sheath 102 is rotatingly disposed about the balloon 114 and a proximal portion 140 of the secondary guidewire housing 104 is engaged to a rotating collar 150.

The collar 150 is engaged to the proximal portion 140 of the secondary guidewire housing 104 by any engagement mechanism desired, such as welding, bonding, mechanical engagement, adhesive engagement, etc. As shown in FIG. 4 for example, the proximal portion 140 of the secondary guidewire housing 104 and the collar 150 are engaged externally at engagement site 142. Alternatively, the secondary guidewire housing 104 may be passed at least partially through the collar 150, and/or the collar 150 may define a lumen through which the secondary guidewire 108 may be passed before entering into the secondary guidewire housing 104.

Collar 150 may be a substantially cylindrical member that is disposed about the shaft 144 of the catheter 116 at a position proximal of the balloon 114. The collar 150 may be characterized as defining a catheter shaft lumen 146 through which the catheter shaft 144 is passed. In order to provide the collar 150 with the ability to freely rotate about the catheter shaft 144, the collar 150 defines a catheter shaft lumen 146 which has a diameter greater than the outer diameter of the shaft 144. In some embodiments one or more lubricious substances may be placed between the collar 150 and the shaft 144 to further encourage free rotation therebetween.

While the rotating collar 150 is free to rotate about the shaft 144, in some embodiments it will also be capable of being longitudinally displaced along the shaft 144 as well. As such, in some embodiments one or more locks or hubs 152 may be affixed about the shaft 144 on one or both sides of the collar 150 to prevent or limit the potential longitudinal displacement of the collar 150 relative to the shaft 144. In some embodiments the use of hubs 152 may be avoided or supplemented by providing the catheter shaft 144 with an annular protrusion or ring 139 which the collar 150 may be disposed about to prevent the assembly 100 from experiencing substantial longitudinal migration.

Figure 10:
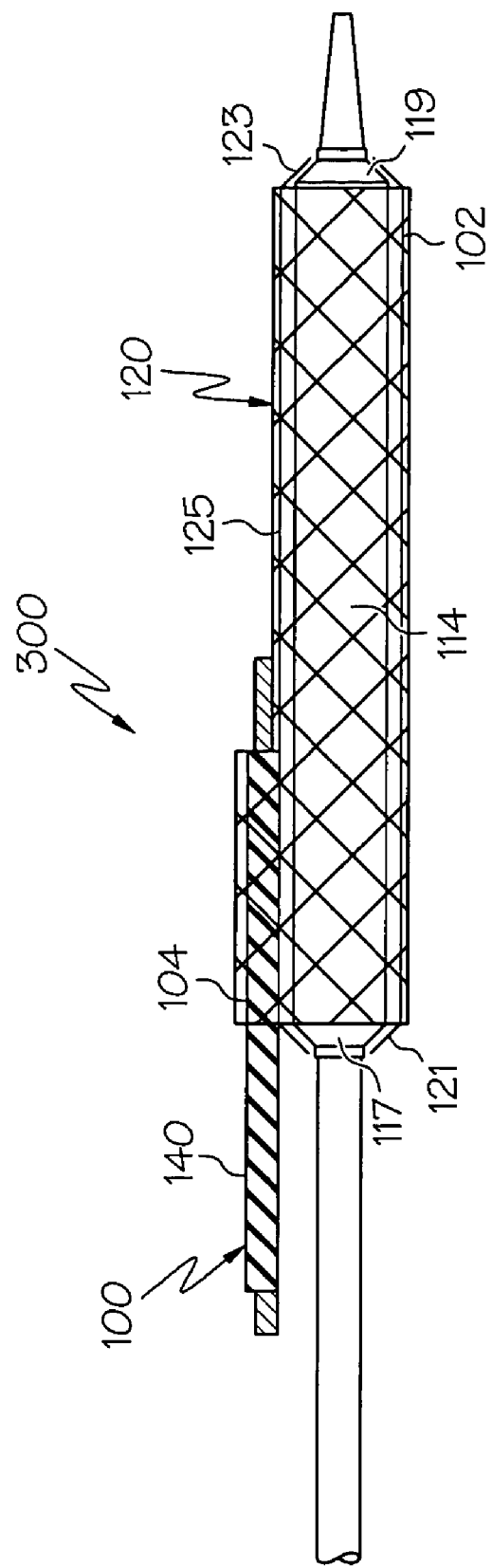
FIG. 10 is a side view of a catheter assembly wherein the sheath of the rotatable assembly extends over the cones of the balloon.

In at least one embodiment, an example of which is shown in FIG. 10, the sheath 102 may be configured to limit longitudinal displacement of the assembly 100 by having a length sufficient to allow one or both ends 121 and 123 of the sheath 102 to extend over the respective cones 117 and 119 of the balloon 114. In some embodiments, each of the end portions 121 and 123 of the sheath 102 have an inner diameter that is less than the inner diameter of the intermediate portion 125. The reduced diameter of the ends 121 and 123 allows the sheath 102 to abut the cones 117 and 119 and/or waists of the balloon 114, while retaining the ability of the sheath 102 to freely rotate about the balloon 114. As a result of the complementary shape and diameter of the end portions 121 and 123 of the sheath to the cones 117 and 119 of the balloon 114 the sheath 102 and thus the entire assembly 100 remains longitudinally in place about the balloon 114 during advancement of the system 300.

In some embodiments, end portions 121 and 123 may be constructed of a material different from that of the intermediate portion 125. In at least one embodiment one or both end portions 121 and 123 are at least partially constructed of a material having a higher hardness or durometer value than that of the material from which the intermediate portion 125 is primarily constructed.

A sheath 102 having end portions 121 and 123 may be utilized with other longitudinal position retention devices such as hubs 152 as discussed above. However, because the sheath 102 may provide the assembly 100 with the desired longitudinal securement about the catheter 116 the use of retaining hubs may be avoided if desired.

In some embodiments the assembly 100 and particularly the sheath 102 may be provided with one or more marker areas or bands 135. Bands 135 may be integral to the construction of the sheath 102 or other portion of the assembly 100 or they may be distinct components and/or coatings that are placed on, about, or within a portion of the assembly 100 following or during its construction. A marker band will typically be at least partially constructed of a material having a higher degree of radiopacity than the material from which the remainder of the assembly 100 is constructed. Such radiopaque materials include gold, platinum, chrome cobalt alloy, etc. In some embodiments the marker bands 135 are at least partially constructed of a material detectable by imaging modalities such as X-Ray, MRI or ultrasound. In at least one embodiment a marker band 135 or the sheath 102 include air voids to ease detection by ultrasound.

In some embodiments such as in the examples shown in FIG. 11, the sheath 102 includes bands 135 at the end regions of the sheath 102 as well as along a circumference of the sheath corresponding to the distal end region of the secondary guidewire housing 104. Furthermore, the placement of bands 135 may be provided to correspond to the ends of the stent 120 as well as the position of the secondary opening 130a, such as in the manner shown in FIG. 12.

In some embodiments at least a portion of the secondary guidewire housing 104 includes a marker band 135.

As has been discussed above, in some embodiments the assembly 100 is provided with a sheath 102 which is configured to be able to freely rotate about a balloon 114 or other portion of a catheter 116. To provide improved rotational freedom, in some embodiments, such as in the examples shown in FIGS. 13a and 13b the sheath 102 may be constructed so that only selected portion of the sheath 102 are in regular contact with the balloon 114 once the system 300 is fully assembled and in use.

Figure 13B:
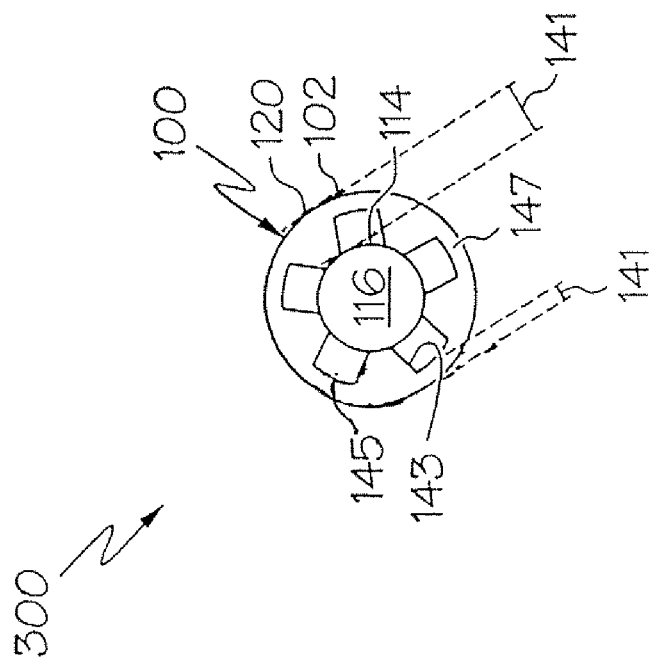
FIG. 13b is a cross-sectional view of a catheter assembly shown in FIG. 4 taken along cross-section "B", wherein the sheath of the rotatable assembly is provided with a variable thickness and inner diameter.
Figure 13A:
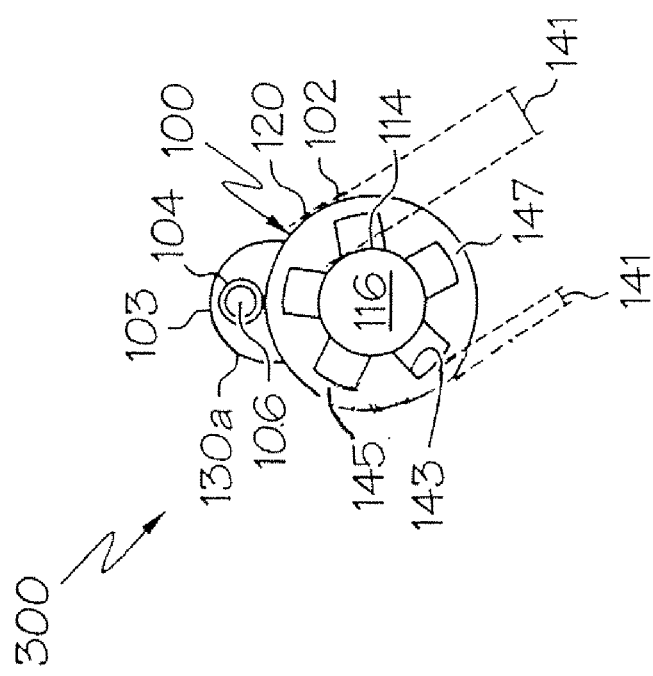
FIG. 13a is a cross-sectional view of a catheter assembly shown in FIG. 4 taken along cross-section "A", wherein the sheath of the rotatable assembly is provided with a variable thickness and inner diameter.

In some embodiments the engagement between the sheath 102 and the balloon 114 is limited by providing the sheath 102 with a variable thickness 141 that provides the inner surface 143 of the sheath 102 with a variable diameter. As shown in FIGS. 13a and 13b the variable thickness 141 of the sheath 102 provides the inner surface 143 with a plurality of peaks 145 and troughs 147, such that when the sheath 102 is rotatably disposed about the balloon 114, contact of the sheath 102 on the balloon 114 is substantially limited to the peaks 145. In some embodiments each peak 145 is in tangential contact with the surface of the balloon 114 prior to delivery.

Figure 14:
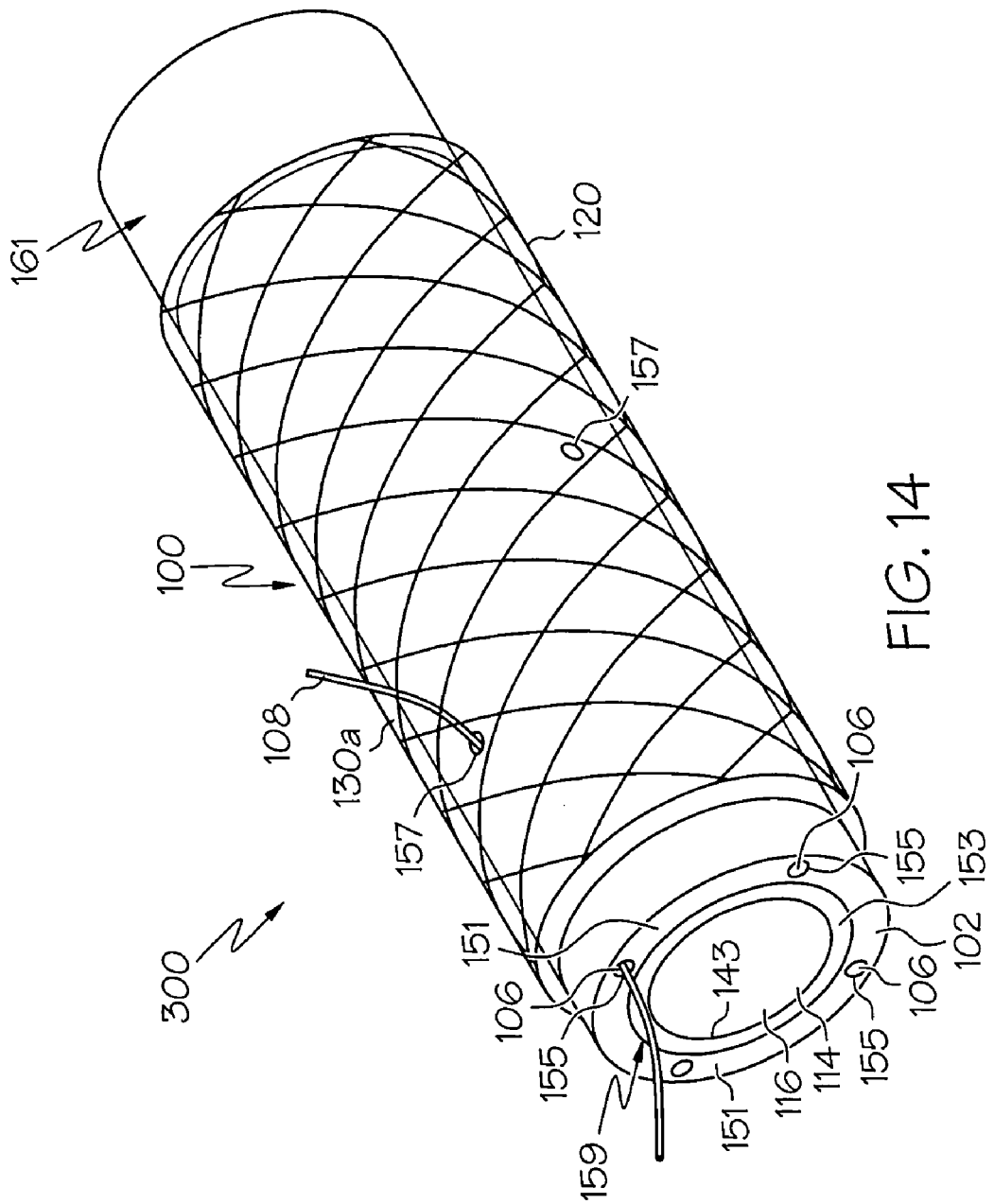
FIG. 14 is a perspective view of an embodiment of the rotatable sheath, with a stent disposed thereabout, shown prior to mounting on a catheter.

In some embodiments of the invention, an example of which is depicted in FIG. 14, the use of a separate and distinct secondary guidewire housing, such as has been described above, may be unnecessary as the sheath 102 may be configured to define one or more a secondary guidewire lumens 106 within the wall 151 of the sheath 102. In the embodiment shown in FIG. 14, the sheath 102 itself defines a primary lumen 153 into which the catheter and/or balloon is positioned as previously discussed, but may best be seen in FIG. 15, within the wall 151 of the sheath 102 one or more secondary lumens 106 is also present.

Lumens 106 may be formed as an integral part of the wall 151 by molding or otherwise directly forming the lumens 106 into the wall 151 during manufacture of the sheath 102. Alternatively, a lumen 106 may be formed by cutting, ablating, boring or otherwise removing material from the wall 151 in order to form the lumen 106 and openings.

Each lumen 106 includes a proximal opening 155 and at least one distal opening 157 in communication therewith. Openings 155 and 157 may be present on the wall's cross-sectional end surface 159, the inner surface 143 and/or the outer surface 161 in order to provide a secondary guidewire 108 with a variety of lumen entrance and exit options.

Each lumen 106 may have a length which extends through the entire longitudinal length of the sheath 102 or only a portion thereof.

As depicted in FIG. 14, by providing the sheath 102 with a variety of secondary lumens 106 as well as by providing individual secondary lumens 106 with multiple distal openings 157, the assembly 100 is able to provide the secondary guidewire 108 with passage to any of a variety of potential secondary opening 130a positions on the stent 120.

By including the secondary guidewire lumen 106 directly into the wall 151 of the sheath 102, the profile of the assembly is desirably reduced. As indicated above, in some procedures where the stent 120 is to be deployed at a vessel bifurcation, such as depicted in FIGS. 5 and 9 it may be desirable to provide the stent with a more pronounced secondary opening and/or passage in order to accommodate subsequent deployment of a second catheter and/or stent therethrough. In such a case the use of a secondary guidewire housing 104, such as has been previously described, may be used to provide a secondary guidewire lumen 106 external of the sheath 102, as in the manner discussed above and shown in FIGS. 1 and 2.

Figure 16A:
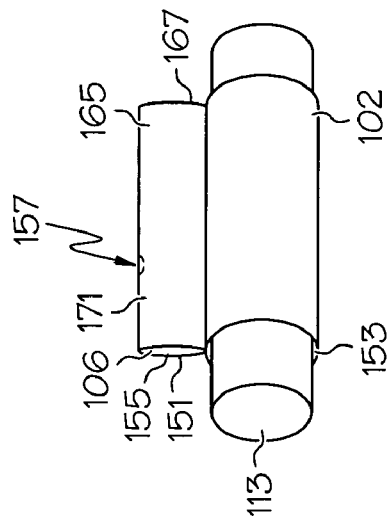
Figure 16B:
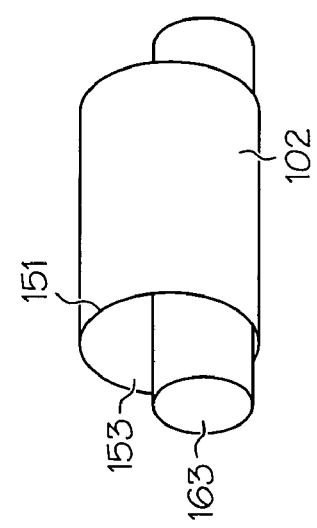

However, it is also noted that an alternative method may be used to provide the assembly 100 with a separate guide wire lumen 106 that is distinct from the primary lumen 153 of the sheath 102, but which is also not an integral passage through the wall 151 of the sheath 102. Such a method is depicted in FIGS. 16a-16d, wherein the secondary guidewire lumen 106 is formed by pinching an area 165 of the sheath 102 together in order to form two adjacent lumens 153 and 106 which extend therethrough. As shown in FIGS. 16A and 16B a mandrel 163 is passed through the primary lumen 153 of the sheath 102. Typically, the mandrel 163 will have an outer diameter that is similar to that of the catheter and/or balloon to which the sheath 102 is to be eventually mounted on. Once the mandrel 163 is in place a radial portion or flap 165 is pinched or folded together along a longitudinal seam 167. Along the seam 167 the portions of the wall 151 which are in contact may be welded, adhered, or otherwise engaged together to form the secondary guidewire lumen 106 and the primary lumen 153.

Figure 16C:
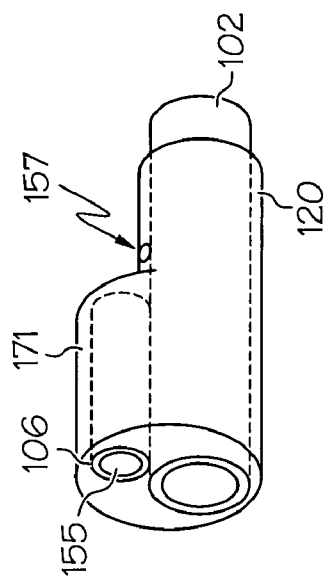
Figure 16D:
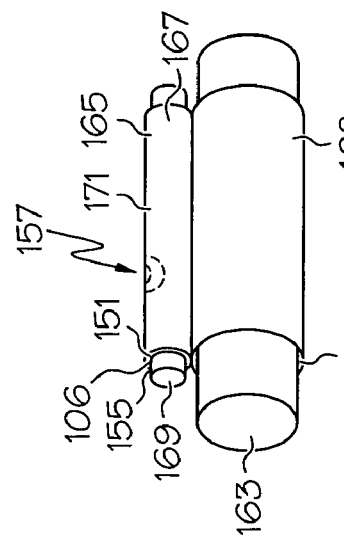

At some point, one or more holes or openings, such as is depicted in FIGS. 16b-16d, may be cut through the wall 151 of the sheath 102 to provide the secondary guidewire lumen 106 with a distal opening 157.

As shown in FIG. 16C, a secondary mandrel 169 may be utilized to support the secondary guidewire lumen 106 during the formation process. The secondary mandrel 169 may extend through the entire length of the sheath 102 or may extend only through a proximal portion 171 of the sheath 102, which extends from the proximal opening 155 to the distal opening 157 of the newly formed secondary guidewire lumen 106.

In some embodiments the sheath 102 is heat set before the mandrels 163 and 169 are removed.

The portion of the radial flap 165 that is distal of the distal opening 157 may be cut away from the sheath 102 along the seam 167 or simply folded underneath the stent 120, when the stent 120 is disposed about the sheath 102 as in the manner shown in FIG. 16D.

Though the secondary guidewire may be passed directly through the secondary guidewire lumen 106 depicted in FIG. 16D, the secondary guidewire lumen 106 may be sufficiently sized to allow passage of a hypotube or other member if desired.

Typically, when producing a system 300, such as is depicted in FIG. 4, the stent 120 is crimped or otherwise reduced in diameter to be properly positioned or seated about the rotatable sheath 102. In some embodiments the stent 120 is crimped by a crimping apparatus once it is positioned about the sheath 102, prior to or subsequent to loading the assembly 100 onto the catheter 116. In some cases however, the rotatable sheath 102 may be configured to retain the stent 120 thereabout without the need to crimp the stent 120 onto the sheath 102.

In at least one embodiment, an example of which is depicted in FIGS. 17A-17C, the sheath 102 is stretched or otherwise elongated in a longitudinal direction in order to reduce the outer diameter of the sheath 102 from a nominal diameter shown in FIG. 17A to a reduced diameter shown in FIG. 17B. When in the reduced diameter state shown in FIG. 17B the stent 120 is placed over the sheath 102 in the manner shown. Once the stent 120 is positioned at a desired location along the sheath 102, the sheath 102 is released from its reduced diameter, longitudinally elongated state shown in FIG. 17B to return to the nominal diameter state shown in FIG. 17C. Due to the relatively soft construction of the outer surface of the sheath 102 as compared to the stent 120, and further because the stent 120 is already in a reduced or crimped diameter state when the sheath 102 is allowed to return to the nominal diameter, the portion of the sheath 102 which underlies the stent 120 will engage the various strut members 132 of the stent 120. Depending on the hardness of the sheath 102, when the sheath 102 is retuned to its nominal diameter under the stent 120, portions of the outer surface of the sheath 102 my form 'bumps' or raised portions 175 which extend radially into the cells 130 of the stent 120. In effect the stent 120 becomes somewhat embedded into the outer surface of the sheath 102.

In some embodiments the stent 120 is disposed about the sheath 102, the combined sheath and stent may be placed in a 'clam shell' or other assembly which restricts radial expansion of the stent, and then the sheath is expanded by balloon or other device in order to form a more distinct interface between the raised portion 175 and the cells 130.

In some embodiments, when a pre-crimped stent 120 is mounted on a rotatable sheath 102 such as in the manner shown in FIGS. 17A-17C, the outer diameter of the stent 120 is substantially the same as the outer diameter of the end portions 121 and 123 of the rotatable sheath 102 which are adjacent thereto. In some embodiments the outer diameter of the stent 120 is less than the outer diameter of the end portions 121 and 123 of the rotatable sheath 102 which are adjacent thereto. By positioning the stent 120 on a sheath 102 which has end portions 121 and 123 having outer diameters that are the same or smaller that the outer diameter of the stent 120, edges of the stent 120 are protected during advancement of the catheter system 300 as depicted in FIG. 5.

While edge protection of the stent 120 is desirable, it is also desirable to provide the system 300 with reduced profile. In at least one embodiment the profile of the system 300 is reduced by providing a mechanism which allows the stent 120 to rotate directly about the catheter 116 without the need for the rotatable sheath 102 between the balloon 114 and the stent 120. Examples of some embodiments, wherein the rotatable sheath 102 is not positioned under the stent 120 are depicted in FIGS. 18-20.

As is shown in FIG. 18, the system 300 may employ a rotatable assembly 100 that includes a rotatable sheath 102 which is rotatably disposed about the catheter shaft 144 proximal to the stent 120 and/or balloon 114. The sheath 102 in this embodiment behaves in a manner very similar to that of the collar (150) such as has been previously described and may be adjacent to one or more hubs 152 or other members (such as a annular ring 139) which aid in limiting longitudinal displacement of the assembly 100 along the shaft 144. The sheath 102 may be engaged to the secondary guidewire housing 104 at one or more engagement sites 142. In addition longitudinal displacement of the stent 120 may be reduced by crimping the portion of the stent that overlays the secondary guidewire housing 104 thereto. If desired the secondary guidewire housing 102 may be provided with a relatively soft or textured surface to better interface or engage the stent 120.

In order to provide the reduced diameter stent 120 with the capacity to freely rotate about the catheter shaft 144 and/or balloon 114 the stent 120, prior to delivery, has a diameter which is greater than that of the catheter shaft 144 and/or balloon 114. As a consequence however, the stent 120 is free to migrate longitudinally along the catheter 116. In order to prevent such migration or dislocation the sheath 102 is engaged to the stent 120. As shown in FIGS. 18-19 the distal end region of the sheath 102 is engaged to the proximal end region of the stent 120 by one or more engagement members 172.

Engagement members 172 may be constructed of any material desired, but are preferably constructed of one or more biocompatible polymers and/or metals. Engagement members 172 have a proximal end portion 174 which is engaged to the sheath 102. A distal end 176 is releasably engaged to one or more struts 132 of the stent 120. During advancement of the system 300 the distal ends 176 of the engagement members 172 are engaged to the stent 120 thereby preventing the stent 120 from being longitudinally displaced relative to the catheter shaft 144. When the stent 120 is expanded for deployment, the distal ends 176 release the stent such as in the manner depicted in FIG. 20.

The engagement members 172 may be at least partially bio-absorbable and thus configured to release the stent 120 upon absorption of the members 172 by the body.

The engagement members 172 may be mechanically actuatable from an engaged position, wherein the stent 120 is retained to the sheath 102, such as in the manner shown in FIG. 18; to an unengaged position, wherein the stent 120 is released from the sheath 102, such as in the manner shown in FIG. 20. Actuation of the members 172 may be a result of the expansion of the stent, and thus dislocation of the engaged struts 132 from the distal ends 176 of the engagement members 172. Alternative forms of mechanical actuation may also be utilized.

In some embodiments the engagement members 172 are at least partially constructed from an EAP material, such as polypyrole, carbon nanotubes (i.e. 'Bucky paper'), etc. Such members are actuatable from the engaged position to the unengaged position by transmitting an electric signal to the engagement members. Such a signal may be transmitted along a conductive catheter shaft 144, or a conductive member included therewith, to the sheath 102 and eventually to the engagement members 172. In such an embodiment the sheath 102 may also include a conductive material in its construction in order to facilitate transmission of the electric signal to the EAP of the engagement members 172.

In some embodiments, such as in the example shown in FIG. 19, the stent 120 is rotatable about a balloon 114, but at least one of material 178 may be positioned between the stent 120 and the balloon 114 to provide additional protection to the balloon 114 and to reduce potential friction between the stent 120 and the balloon. Layer or layers 178 may be a lubricious coating, a protective membrane, etc. which may be utilized to provide the balloon 114 and stent 120 with enhanced protection, reduced friction, and/or any other desirable characteristic.

The invention has been described with reference to the embodiments. Obviously, modifications and alterations will occur to others upon a reading and understanding of this specification. For example, the illustrated embodiments use a balloon to expand the stent although, as briefly noted above, a self expanding, self deploying or hybrid expandable stent can be used without departing from the features of the present invention. The invention is intended to include all such modifications and alterations thereof.

Furthermore, it is noted that the various embodiments shown and described in U.S. patent application Ser. No. 10/375,689, filed Feb. 27, 2003 and U.S. patent application Ser. No. 10/657,472, filed Sep. 8, 2003, both of which are entitled Rotating Balloon Expandable Sheath Bifurcation Delivery, may be incorporated and/or utilized with the various embodiments described herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
   a catheter, the catheter comprising a catheter shaft and a balloon positioned at a distal end portion of the catheter shaft, the balloon including a first portion having a first outer diameter and a second portion having a second outer diameter that is different than the first outer diameter;
   a rotatable sheath, the rotatable sheath rotatably disposed about at least a portion of the balloon, the rotatable sheath including a first portion having a first portion inner diameter and a second portion having a second portion inner diameter that is different than the first portion inner diameter, the first portion of the rotatable sheath being arranged axially adjacent the second portion of the rotatable sheath, the first portion of the rotatable sheath arranged in radial alignment with the first portion of the balloon and the second portion of the rotatable sheath arranged in radial alignment with the second portion of the balloon such that the rotatable sheath is longitudinally secured relative to the balloon when the balloon is in both an expanded state and an unexpanded state; and
   a guidewire housing, the guidewire housing defining a guidewire lumen for passage of a guidewire therethrough, at least a portion of the guidewire housing being engaged to an outer surface of the rotatable sheath.

2. The catheter assembly of claim 1 wherein at least a portion of the guidewire housing is engaged to at least a proximal portion of the outer surface of the rotatable sheath.

3. The catheter assembly of claim 1 further comprising a stent, the stent being disposed about at least a portion of the rotatable sheath.

4. The catheter assembly of claim 3 wherein at least a portion of the stent is disposed about at least a portion of the guidewire housing.

5. The catheter assembly of claim 1 wherein the rotatable sheath further comprises a third portion, at least the second portion of the rotatable sheath being positioned between the first portion and the third portion of the rotatable sheath, the first portion inner diameter being less than the second portion inner diameter.

6. The catheter assembly of claim 5 wherein the rotatable sheath comprises a length, the second portion inner diameter being substantially constant along the length of the second portion.

7. The catheter assembly of claim 6 wherein the first portion inner diameter is tapered along the length of the first portion.

8. The catheter assembly of claim 6 wherein the third portion defines a third portion inner diameter, the third portion inner diameter being less than the second portion inner diameter.

9. The catheter assembly of claim 8 wherein the third portion inner diameter is tapered along the length of the third portion.

10. The catheter assembly of claim 1 further comprising a stent, the stent being disposed about at least a portion of the rotatable sheath, the stent comprising a plurality of interconnected stent members wherein adjacent members define cell openings.

11. The catheter assembly of claim 10 wherein the rotatable sheath comprises a first end portion, a second end portion and an intermediate portion therebetween, the stent being disposed about the intermediate portion of the rotatable sheath, the first end portion having a first end portion outer diameter, the second end portion having a second end portion outer diameter, the intermediate portion having an intermediate portion outer diameter, the stent having a stent outer diameter, at least one of the first end portion outer diameter and the second end portion outer diameter being at least as great as the stent outer diameter.

12. The catheter assembly of claim 11 wherein the first end portion outer diameter and the second end portion outer diameter are substantially equal to the stent outer diameter.

13. The catheter assembly of claim 10 wherein at least a portion of the stent is coated with at least one therapeutic agent.

14. The catheter assembly of claim 13 wherein the at least one therapeutic agent is at least one non-genetic therapeutic agent selected from at least one member of the group consisting of: anti-thrombogenic agents; anti-proliferative agents; anti-inflammatory agents; antineoplastic/antiproliferative/anti-miotic agents; anesthetic agents; anti-coagulants; vascular cell growth promoters; vascular cell growth inhibitors; bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

15. The catheter assembly of claim 14 wherein the at least one therapeutic agent comprises at least one anti-thrombogenic agent selected from at least one member of the group consisting of: heparin, heparin derivatives, urokinase, and PPack (dextrophenylalanine praline arginine chloromethylketone).

16. The catheter assembly of claim 14 wherein the at least one therapeutic agent comprises at least one anti-proliferative agent selected from at least one member of the group consisting of: enoxaprin, angiopeptin, monoclonal antibodies capable of blocking smooth muscle cell proliferation, hirudin, and acetylsalicylic acid.

17. The catheter assembly of claim 14 wherein the at least one therapeutic agent comprises at least one anti-inflammatory agent selected from at least one member of the group consisting of: dexamethasone, prednisolone, corticosterone, budesonide, estrogen, sulfasalazine, and mesalamine.

18. The catheter assembly of claim 14 wherein the at least one therapeutic agent comprises at least one anesthetic agent selected from at least one member of the group consisting of: lidocaine, bupivacaine and ropivacaine.

19. The catheter assembly of claim 14 wherein the at least one therapeutic agent comprises at least one anti-coagulant selected from at least one member of the group consisting of: D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides.

20. The catheter assembly of claim 14 wherein the at least one therapeutic agent comprises at least one vascular cell growth promoters selected from at least one member of the group consisting of: growth factor inhibitors, growth factor receptor antagonists, transcriptional activators, and translational promoters.

21. The catheter assembly of claim 14 wherein the at least one therapeutic agent comprises at least one vascular cell growth inhibitor selected from at least one member of the group consisting of: growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin.

22. The catheter assembly of claim 14 wherein the at least one therapeutic agent comprises at least one antineoplastic/antiproliferative/anti-miotic agent selected from at least one member of the group consisting of: paclitaxel, 5-fluorouracil, cisplatin, vinblastine, vincristine, epothilones, endostatin, angiostatin and thymidine kinase inhibitors.

23. The catheter assembly of claim 13 wherein the at least one therapeutic agent is at least one genetic therapeutic agent selected from at least one member of the group consisting of: anti-sense DNA and RNA; DNA coding for anti-sense RNA, tRNA or rRNA to replace defective or deficient endogenous molecules; angiogenic factors including growth factors; cell cycle inhibitors including CD inhibitors, thymidine kinase ("TK") and other agents useful for interfering with cell proliferation; at least one of the family of bone morphogenic proteins ("BMP's"); dimeric proteins; molecules capable of inducing an upstream or downstream effect of a BMP, or the DNA's encoding them and any combinations thereof.

24. The catheter assembly of claim 23 wherein the at least one therapeutic agent comprises at least one growth factor selected from at least one member of the group consisting of: acidic and basic fibroblast growth factors, vascular endothelial growth factor, epidermal growth factor, transforming growth factor a and /3, platelet-derived endothelial growth factor, platelet-derived growth factor, tumor necrosis factor a, hepatocyte growth factor and insulin like growth factor.

25. The catheter assembly of claim 23 wherein the at least one therapeutic agent comprises at least one of the family of bone morphogenic proteins ("BMP's") selected from at least one member of the group consisting of: BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16.

26. The catheter assembly of claim 23 wherein the at least one therapeutic agent comprises at least one dimeric proteins selected from at least one member of the group consisting of: homodimers, heterodimers, or combinations thereof.

27. The catheter assembly of claim 13 wherein the at least one therapeutic agent is at least one type of cellular material selected from at least one member of the group consisting of: cells of human origin (autologous or allogeneic); cells of non-human origin (xenogeneic) and any combination thereof.

28. The catheter assembly of claim 27 wherein the cellular material is selected from at least one member of the group consisting of: side population cells; lineage negative cells; lineage negative $CD34^-$ cells; lineage negative $CD34^+$ cells; lineage $negative^- cKit^+$ cells; mesenchymal stem cells; cord blood bells; cardiac or other tissue derived stem cells; whole bone marrow; bone marrow mononuclear cells; endothelial progenitor cells; satellite cells; muscle derived cells; go cells; endothelial cells; adult cardiomyocytes; fibroblasts; smooth muscle cells; cultures of mesenchymal stem cells with 5-aza forces differentiation into cardiomyocytes; adult cardiac fibroblasts+5-aza; genetically modified cells; tissue engineered grafts; MyoD scar fibroblasts; Pacing cells; embryonic stem cell clones; embryonic stem cells; fetal or neonatal cells; immunologically masked cells; tissue engineered grafts; genetically modified cells; teratoma derived cells and any combinations thereof.

29. The catheter assembly of claim 13 wherein the at least one therapeutic agent comprises at least one polymer coating, the at least one coating selected from at least one member of the group consisting of: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions; polysaccharides; hyaluronic acid; squalene emulsions; polyacrylic acid, a copolymer of polylactic acid and polycaprolactone; medical-grade biodegradable materials; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$^4$'s; cyanoacrylate; 50/50 DLPLG; polydioxanone; polypropylene fumarate; polydepsipeptides; chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; A block copolymers; B block copolymers and any combinations thereof.

30. The catheter assembly of claim 1 further comprising a lubricious coating, the lubricious coating positioned between at least a portion of the rotatable sheath and the catheter shaft.

31. The catheter assembly of claim 1 wherein the rotatable sheath is at least partially constructed from a hydrophilic polymer material.

32. The catheter assembly of claim 1 wherein the rotatable sheath is at least partially constructed from a tecophilic material.

33. The catheter assembly of claim 1 wherein the rotatable sheath is at least partially constructed from a first material and a second material.

34. The catheter assembly of claim 33 wherein the rotatable sheath is at least partially constructed from at least one material of the group consisting of hydrophilic polyurethanes, aromatic polyurethanes, polycarbonate base aliphatic polyurethanes, engineering polyurethane, elastomeric polyamides, block polyamide/ethers, polyether block amide, silicones, polyether-ester, polyester, polyester elastomer, polyethylene, polyamide, high-density polyethylene, polyetheretherketone, polyimide, polyetherimide, liquid crystal polymers, acetal, and any combination thereof.

35. The catheter assembly of claim 33 wherein the first material is a polymer matrix and the second material is at least one distinct member of reinforcing material at least partially supported within the polymer matrix.

36. The catheter assembly of claim 35 wherein polymer matrix is selected from at least one material from the group consisting of: hydrophilic polyurethanes, aromatic polyurethanes, polycarbonate base aliphatic polyurethanes, engineering polyurethane, elastomeric polyamides, block polyamide/ethers, polyether block amide, silicones, polyether-ester, polyester, polyester elastomer, polyethylene and any combination thereof.

37. The catheter assembly of claim 35 wherein the reinforcing material is selected from at least one material of the group consisting of polyamide, polyethylene, high-density polyethylene, polyetheretherketone, polyimide, polyetherimide, liquid crystal polymers, acetal, and any combination thereof.

38. The catheter assembly of claim 1 wherein the rotatable sheath has a length substantially less than a length of the catheter.

39. A catheter assembly comprising:
a catheter shaft;
a balloon, the balloon arranged on the catheter shaft and having at least a first tapered end and a second tapered end; and
a rotatable sheath, the rotatable sheath rotatably disposed about at least a portion of the balloon, the rotatable sheath including a first radially tapered end that is arranged in radial alignment with the first tapered end of the balloon and a second tapered end that is arranged in radial alignment with the second tapered end of the balloon, the first radially tapered end of the rotatable sheath being configured to complement the first tapered end of the balloon, the second tapered end of the rotatable sheath being configured to complement the second tapered end of the balloon, wherein the first and second tapered ends being configured to complement the first and second tapered ends of the balloon and longitudinally secure the rotatable sheath relative to the balloon when the balloon is in an expanded state and an unexpanded state.

40. The catheter assembly of claim 39, further comprising a stent, the stent being disposed about at least a portion of the rotatable sheath.

41. The catheter assembly of claim 39 further comprising a guidewire housing, the guidewire housing defining a guidewire lumen for passage of a guidewire therethrough, at least a portion of the guidewire housing being engaged to a portion of an outer surface of the rotatable sheath.

42. The catheter assembly of claim 39 wherein the first and second radially tapered ends of the rotatable sheath include a material having a higher hardness value than a portion of the rotatably sheath between the first and second radially tapered ends.

* * * * *

UNITED STATES PATENT AND TRADEMARK OFFICE
CERTIFICATE OF CORRECTION

| | | |
|---|---|---|
| PATENT NO. | : 7,922,753 B2 | Page 1 of 1 |
| APPLICATION NO. | : 10/757646 | |
| DATED | : April 12, 2011 | |
| INVENTOR(S) | : Eidenschink et al. | |

It is certified that error appears in the above-identified patent and that said Letters Patent is hereby corrected as shown below:

Column 20
Line 44: delete "factor a and", and insert therefor -- factor α and --.
Line 45: delete "necrosis factor a", and insert therefor -- necrosis factor α --.

Signed and Sealed this
Thirty-first Day of May, 2011

David J. Kappos
*Director of the United States Patent and Trademark Office*